US005672683A

United States Patent [19]
Friden et al.

[11] Patent Number: 5,672,683
[45] Date of Patent: Sep. 30, 1997

[54] TRANSFERRIN NEUROPHARMACEUTICAL AGENT FUSION PROTEIN

[75] Inventors: Phillip M. Friden, Bedford; Ruth M. Starzyk, Framingham, both of Mass.; Sherie L. Morrison, Los Angeles, Calif.; Eun-Chung Park, Cambridge, Mass.

[73] Assignees: Alkermes, Inc., Cambridge, Mass.; The Regents of the University of California, Los Angeles, Calif.

[21] Appl. No.: 94,534

[22] Filed: Jul. 16, 1993

Related U.S. Application Data

[60] Continuation-in-part of Ser. No. 999,803, Nov. 20, 1992, abandoned, which is a division of Ser. No. 846,830, Mar. 6, 1992, Pat. No. 5,182,107, which is a continuation-in-part of Ser. No. 404,089, filed as PCT/US90/05077, Sep. 7, 1990, Pat. No. 5,154,924.

[51] Int. Cl.$^6$ .................. C07K 14/00; C07K 14/475
[52] U.S. Cl. .................. 530/350; 530/399; 530/402; 435/697; 536/23.4
[58] Field of Search .................. 530/350, 399, 530/402; 435/69.1, 69.7; 536/23.4

[56] References Cited

U.S. PATENT DOCUMENTS

| | | | |
|---|---|---|---|
| 4,292,425 | 9/1981 | Buckler et al. | 536/4 |
| 4,434,156 | 2/1984 | Trowbridge | 424/85 |
| 4,444,744 | 4/1984 | Goldenberg | 424/1.1 |
| 4,545,985 | 10/1985 | Pastan et al. | 424/85 |
| 4,569,789 | 2/1986 | Blattler et al. | 260/112 |
| 4,626,507 | 12/1986 | Trowbridge et al. | 435/240 |
| 4,631,190 | 12/1986 | Shen et al. | 424/85 |
| 4,801,575 | 1/1989 | Pardridge | 514/4 |
| 4,816,567 | 3/1989 | Cabilly et al. | 530/387 |
| 4,886,780 | 12/1989 | Faulk | 514/8 |
| 4,892,827 | 1/1990 | Pastan et al. | 435/193 |
| 4,902,505 | 2/1990 | Pardridge | 424/85.7 |
| 4,992,255 | 2/1991 | Pardridge | 424/1.1 |
| 5,004,697 | 4/1991 | Pardridge | 436/547 |
| 5,026,651 | 6/1991 | Bowman et al. | 435/320.1 |
| 5,028,697 | 7/1991 | Johnson et al. | 530/388 |
| 5,087,616 | 2/1992 | Meyers et al. | 514/21 |
| 5,091,513 | 2/1992 | Huston et al. | 530/387 |
| 5,108,987 | 4/1992 | Faulk | 514/8 |
| 5,130,129 | 7/1992 | Pardridge | 424/85.8 |
| 5,132,405 | 7/1992 | Huston et al. | 530/387 |
| 5,141,736 | 8/1992 | Iwasa et al. | 530/387 |
| 5,169,764 | 12/1992 | Shooter et al. | 435/69.7 |

FOREIGN PATENT DOCUMENTS

| | | |
|---|---|---|
| 0 094 844 | 11/1983 | European Pat. Off. . |
| 0 175 560 | 3/1986 | European Pat. Off. . |
| 0196056 | 10/1986 | European Pat. Off. . |
| 0 253 202 | 1/1988 | European Pat. Off. . |
| 0 286 418 | 10/1988 | European Pat. Off. . |
| 0 286 441 | 10/1988 | European Pat. Off. . |
| 0 305 867 | 3/1989 | European Pat. Off. . |
| 0 324 625 | 7/1989 | European Pat. Off. . |
| 0 327 169 | 8/1989 | European Pat. Off. . |
| 0 328 147 | 8/1989 | European Pat. Off. . |
| 0 336 383 | 10/1989 | European Pat. Off. . |
| 0 449 769 | 10/1991 | European Pat. Off. . |
| 0466222 | 1/1992 | European Pat. Off. . |
| 1 564 666 | 4/1980 | United Kingdom . |
| WO 86/01409 | 3/1986 | WIPO . |
| WO 88/07365 | 10/1988 | WIPO . |
| 91/04753 | 4/1991 | WIPO . |
| 91/09965 | 7/1991 | WIPO . |
| WO91/14438 | 10/1991 | WIPO . |
| 92/13570 | 8/1992 | WIPO . |
| 92/22332 | 12/1992 | WIPO . |
| 93/10819 | 6/1993 | WIPO . |

OTHER PUBLICATIONS

Villa–Komaroff et al., PNAS, vol. 75, pp. 3727–3731, 1978.

Granholm et al., Society for Neurosciences, Abstracts, vol. 18, Part 1, p. 416, No. 183.10, 1992.

Walus et al., J. Cell Biochem Suppl. 15 (Part E) p. 139, N411, 1991.

Kurschner et al., J. of Biol. Chem., vol. 267, pp. 9354–9360, 1992.

Trowbridge, I.S. et al., "Anti–Transferrin Receptor Monoclonal Antibody and Toxin–Antibody Conjugates Affect Growth of Human Tumour Cells", *Nature*, 294(12): 171–173 (Nov. 1981).

Domingo, D.L. et al., "Transferrin Receptor as a Target for Antibody–Drug Conjugates", *Methods in Enzymology*, 112: 238–247 (1985).

Zovickian, J. et al., "Potent and Specific Killing of Human Malignant Brain Tumor Cells by an Anti–Transferrin Receptor Antibody–Ricin Immunotoxin", *N. Neurosurg.*, 66: 850–861 (1987).

Jeffries, W.A. et al., "Transferrin Receptor on Endothelium of Brain Capillaries", *Nature*, 312(8): 162–163 (1984).

Raso, V. et al., "Monensin is Obligatory for the Cytotoxic Action of a Disulfide Linked Methotrexate–Anti–Transferrin Receptor Conjugate", *Biochem. Biophys. Res. Comm.*, 150(1): 104–110 (1988).Bjorn, M.J. et al., "Immunotoxins to the Murine Transferrin Receptor: Intracavitary Therapy of Mice Bearing Syngeneic Peritoneal Tumors", *Cancer Research* 47(24, pt. 1): 6639–6645 (Dec. 15, 1971).

(List continued on next page.)

*Primary Examiner*—Stephen Walsh
*Assistant Examiner*—Sally P. Teng
*Attorney, Agent, or Firm*—Hamilton, Brook, Smith & Reynolds, P.C.

[57] ABSTRACT

The present invention pertains to a method for delivering a neuropharmaceutical agent across the blood brain barrier to the brain of a host. The method comprises administering to the host a therapeutically effective amount of a ligand-neuropharmaceutical agent fusion protein wherein the ligand is reactive with a brain capillary endothelial cell receptor. Other aspects of this invention include a delivery system comprising a ligand reactive with a brain capillary endothelial cell receptor which has formed a fusion protein with a neuropharmaceutical agent. The fusion proteins are also aspects of this invention.

11 Claims, 16 Drawing Sheets

OTHER PUBLICATIONS

Smyth, M.J. et al., "The Mode of Action of Methotrexate–Monoclonal Antibody Conjugates" *Immunol. Cell. Biol.*, 65(2): 189–200 (1987).

Pardridge, W.M. "Receptor–Mediated Peptide Transport through the Blood–Brain Barrier", *Endocrine Reviews*, 7(3): 314–330 (1986).

Sutherland, R. et al., "Ubiquitous Cell–Surface Glycoprotein on Tumor Cells is Proliferation–Associated Receptor for Transferrin", *Proc. Nat'l Acad. Sci. USA*, 78(7): 4515–4519 (Jul. 1981).

Shen, W.–C. et al., "CIS–Aconityl Spacer Between Daunomycin and Macromolecular Carriers: A Model of Ph–Sensitive Linkage Releasing Drug from a Lysosomotropic Conjugate" *Biochem. and Biophys. Res. Comm.* 2(3): 1048–1054 (Oct. 15, 1981).

Pietersz, G.A. et al., "Novel Synthesis and in vivo Characterization of Disulfide–linked Ricin–Monoclonal Antibody Conjugates Devoid of Galactose Binding Activity" *Cancer Res.*, 48: 4469–4476 (1988).

Pietersz, G.A. et al., "The Use of Monoclonal Antibody Conjugates for the Diagnosis and Treatment of Cancer" *Immunol. Cell Biol.*, 65(pt. 2): 111–125 (1987).

Gascoigne, N.R.J. et al., "Secretion of a Chimeric T–Cell Receptor–Immunoglobulin Protein" *Proc. Nat'l Acad. Sci. USA* 84: 2936–2940 (1987).

Baldwin, R.W. et al., "Monoclonal Antibodies for Radioimmunodetection of Tumours and for Targeting" *Bull. Cancer* (Paris) 70(2): 132–136 (1983).

Byrn, R.A. et al., "Biological Properties of a CD4 Immunoadhesin" *Nature* 344: 667–670 (1990).

Griffin, T.W. et al., "In Vitro Cytotoxicity of Recombinant Ricin a Chain–Antitransferrin Receptor Immunotoxin Against Human Adenocarcinomas of Colon and Pancreas" *J. Biol. Res. Mod.*, 7: 559–567 (1988).

Alkan, S.S. et al., "Antiviral and Antiproliferative Effects of Interferons Delivered via Monoclonal Antibodies" *J. Interferon Res.*, 4(3): 355–363 (1984).

Capon, D.J. et al., "Designing CD4 Immunoadhesins for AIDS Therapy" *Nature* 337: 525–531 (1989).

Dautry–Varsat, A. et al., "pH and the Recycling of Transferrin During Receptor–Mediated Endocytosis" *Proc. Nat'l Acad. Sci. USA* 80: 2258–2262 (Apr. 1983).

Herz, J. et al., "Low Density Lipoprotein Receptor–related Protein Mediates Endocytosis of Monoclonal Antibodies in Cultured Cells and Rabbit Liver" *J. Biol. Chem.* 265(34): 21355–21362.

Fishman, J.B. et al., "Receptor–Mediated Transcytosis of Transferrin Across the Blood–Brain Barrier" *J. Neur. Res.*, 18: 299–304 (1987).

Pardridge, W.M. et al., "Selective Transport of an Antitransferrin Receptor Antibody through the Blood–Brain Barrier in vivo" *J. Pharmacol. and Exp. Therapeutics* 259(1): 66–70 (1991).

Morrison, S.L. et al., "Genetically Engineered Antibody Molecules: New Tools for Cancer Therapy" *Cancer Investigation* 6(2): 185–192 (1988).

Dangl, J.L et al., "Segmented Flexibility and Complement Fixation of Genetically Engineered Chimeric Human, Rabbit and Mouse Antibodies," *Embo J.*, 7: 1989–1994 (pub. 1988).

Hoogenboom, H.R. et al., "Cloning and Expression of a Chimeric Antibody Directed Against the Human Transferrin Receptor," *J. Immunol.* 144(8): 3211–3217 (Apr. 15, 1990).

Batra, J.K. et al., "Antitumor Activity in Mice of an Immunotoxin Made with Anti–Transferrin Receptor and a Recombinant Form of *Pseudomonas Exotoxin*" *Proc. Natl. Acad. Sci. USA*, 86: 8545–8549 (Nov. 1989).

Batra, J.K. et al., "Single–Chain Immunotoxins Directed at the Human Transferrin Receptor Containing *Pseudomonas* Exotoxin A or Diphtheria Toxin: Anti–TFR(Fv)–PE40 and DT388–Anti–TFR(Fv)" *Molecular & Cellular Biology* 11(4): 2200–2205 (Apr. 1991).

Weber, J.A. and R.A. Weiss, "HIV Infection: The Cellular Picture," In: *The Science of AIDS; Readings from Scientific American Magazine*, W.H. Freeman and Company, NY, pp. 75–84 (Oct. 1988).

Fingl, E. and D.M. Woodbury, (1975), Section I, Introduction; Chapter I, Principles, In: *The Pharmacological Basis of Therapeutics*, Goodman et al., Eds. (Macmillan Publishing Co., Inc.) pp. 1–45 (1975).

Pardridge, W.M. et al., "Human Blood–Brain Barrier Transferrin Receptor," *Metabolism* 36(9): 862–895 (Sep. 1987).

T.A. Waldmann, "Monoclonal Antibodies in Diagnosis and Therapy," *Science* 252: 1657–1662 (Jun. 21, 1991).

Cumber, A.J. et al., "Preparation of Antibody–Toxin Conjugates," *Methods in Enzymology* 112: Academic Press, pp. 207–225 (1985).

Julian, R. et al., "A New Reagent Which May Be Used to Introduce Sulfhydryl Groups into Proteins, and Its Use in the Preparation of Conjugates for Immunoassay," *Analytical Biochemistry* 132: 68–73 (1983).

*The Merck Index*, Ninth Edition, (M. Windholz, eds.) No. 9261, "Transferrins," p. 1230 (1976).

Grob, P.M. et al., "Affinity Labeling and Partial Purification of Nerve Growth Factor Receptors from Rat Pheochromocytoma and Human Melanoma Cells," *Proc. Natl. Acad. Sci. USA* 80: 6819–6823 (Nov. 1983).

Flanagan, P.A. et al., "Evaluation of Protein–N–(2–hydroxypropyl)methacrylamide Copolymer Conjugates as Targetable Drug Carriers . . . " *Biochimica et Biophysica Acta* 993: 83–91 (1989).

H.R. Hoogenboom et al., "Construction and Expression of Antibody–Tumor Necrosis Factor Fusion Proteins," *Mol. Immun.* 28(9): 1027–1037 (1991).

S.M. Rybak et al., "Humanization of Immunotoxins" *Proc. Natl. Acad. Sci. USA* 89: 3165–3169 (Apr. 1992).

M. Cazzola et al., "Cytotoxic Activity of an Anti–Transferrin Receptor Immunotoxin on Normal and Leukemic Human Hematopoietic Progenitors," *Cancer Research* 51: 536–541 (Jan. 15, 1991).

Xho I
CTCGAGATCC ATTGTGCTCT AAAGGAGATA CCCGGCCAGA CACCCTCACC TGCGGTGCC
AGCTGCCCAG GCTGAGGCAA GAGAAGGCCA GAAACC

CD5 Leader

ATGC CCATGGGGTC TCTGCAACCG CTGGCCACCT TGTACCTGCT
GGGGATGCTG GTCGCTTCCG TGCTAGCGGA TCCCGAG

GGT GAGTACTAAG CTTCAGCGCT CCTGCCTGGA CGCATCCCGG CTATGCAGCC
CCAGTCCAGG GCAGCAAGGC AGGCCCCGTC TGCCTCTTCA CCCGGAGCCT CTGCCCGCCC
CACTCATGCT CAGGGAGAGG GTCTTCTGGC TTTTTCCCAG GCTCTGGGCA GGCACAGGCT
AGGTGCCCCT AACCCAGGCC CTGCACACAA AGGGGCAGGT GCTGGGCTCA GACCTGCCAA
GAGCCATATC CGGGAGGACC CTGCCCCTGA CCTAAGCCCA CCCCAAAGGC CAAACTCTCC
ACTCCCTCAG CTCGGACACC TTCTCTCCTC CCAGATTCCA GTAACTCCCA ATCTTCTCTC
TGCA

IgG1 Exon 1

GAGCCC AAATCTTGTG ACAAAACTCA CACATGCCCA CCGTGCCCAG
GTAAGCCAGC CCA

GGCCTCG CCCTCCAGCT CAAGGCGGGA CAGGTGCCCT AGAGTAGCCT GCATCCAGGG
ACAGGCCCCA GCCGGGTGCT GACACGTCCA CCTCCATCTC TTCCTCA

IgG1 Exon 2

GCA CCTGAACTCC TGGGGGGACC GTCAGTCTTC CTCTTCCCCC
CAAAACCCAA GGACACCCTC ATGATCTCCC GGACCCCTGA
GGTCACATGC GTGGTGGTGG ACGTGAGCCA CGAAGACCCT
GAGGTCAAGT TCAACTGGTA CGTGGACGGC GTGGAGGTGC
ATAATGCCAA GACAAAGCCG CGGGAGGAGC AGTACAACAG
CACGTACCGG GTGGTCAGCG TCCTCACCGT CCTGCACCAG
GACTGGCTGA ATGGCAAGGA GTACAAGTGC AAGGTCTCCA
ACAAAGCCCT CCCAGCCCCC ATCGAGAAAA CCATCTCCAA
AGCCAAA

GGT GGGACCCGTG GGGTGCGAGG GCCACATGGA CAGAGGCCGG CTCGGCCCAC
CCTCTGCCCT GAGAGTGACC CTGTACCAA CCTCTGTCCT ACA

IgG3 Exon 3

GGGCAGC CCCGAGAACC ACAGGTGTAC ACCCTGCCCC
CATCCCGGGA TGAGCTGACC AAGAACCAGG TCAGCCTGAC
CTGCCTGGTC AAAGGCTTCT ATCCCAGCGA CATCGCCGTG
GAGTGGGAGA

FIG. 9A

GCAATGGGCA GCCGGAGAAC AACTACAAGA CCACGCCTCC
CGTGCTGGAC TCCGACGGCT CCTTCTTCCT CTACAGCAAG
CTCACCGTGG ACAAGAGCAG GTGGCAGCAG GGGAACGTCT
TCTCATGCTC CGTGATGCAT GAGGCTCTGC ACAACCACTA
CACGCAGAAG AGCCTCTCCC TGTCTCCGGG TAAA
TGAGTG CGACGGCCG
      Eag I

FIG. 9B

TRANSFERRIN NEUROPHARMACEUTICAL AGENT FUSION PROTEIN

RELATED APPLICATIONS

This Application is a Continuation-in-Part of U.S. Ser. No. 07/999,803 filed Nov. 20, 1992, now abandoned, which is a Divisional of U.S. Ser. No. 07/846,830 filed Mar. 6, 1992 (now U.S. Pat. No. 5,182,107), which is a CIP of PCT/US90/05077, filed Sep. 7, 1990, designating the United States which, in turn, is a Continuation-in-Part of U.S. application Ser. No. 07/404,089 filed Sep. 7, 1989 (now U.S. Pat. No. 5,154,924).

BACKGROUND

The capillaries that supply blood to the tissues of the brain constitute the blood brain barrier (Goldstein et al. (1986) *Scientific American* 255:74-83; Pardridge, W. M. (1986) *Endocrin. Rev.* 7:314-330). The endothelial cells which form the brain capillaries are different from those found in other tissues in the body. Brain capillary endothelial cells are joined together by tight intercellular junctions which form a continuous wall against the passive movement of substances from the blood to the brain. These cells are also different in that they have few pinocytic vesicles which in other tissues allow somewhat unselective transport across the capillary wall. Also lacking are continuous gaps or channels running through the cells which would allow unrestricted passage.

The blood-brain barrier functions to ensure that the environment of the brain is constantly controlled. The levels of various substances in the blood, such as hormones, amino acids and ions, undergo frequent small fluctuations which can be brought about by activities such as eating and exercise (Goldstein et al., cited supra). If the brain were not protected by the blood brain barrier from these variations in serum composition, the result could be uncontrolled neural activity.

The isolation of the brain from the bloodstream is not complete. If this were the case, the brain would be unable to function properly due to a lack of nutrients and because of the need to exchange chemicals with the rest of the body. The presence of specific transport systems within the capillary endothelial cells assures that the brain receives, in a controlled manner, all of the compounds required for normal growth and function. In many instances, these transport systems consist of membrane-associated receptors which, upon binding of their respective ligand, are internalized by the cell (Pardridge, W. M., cited supra). Vesicles containing the receptor-ligand complex then migrate to the abluminal surface of the endothelial cell where the ligand is released.

The problem posed by the blood-brain barrier is that, in the process of protecting the brain, it excludes many potentially useful therapeutic agents. Presently, only substances which are sufficiently lipophilic can penetrate the blood-brain barrier (Goldstein et al., cited supra; Pardridge, W. M., cited supra). Some drugs can be modified to make them more lipophilic and thereby increase their ability to cross the blood brain barrier. However, each modification has to be tested individually on each drug and the modification can alter the activity of the drug. The modification can also have a very general effect in that it will increase the ability of the compound to cross all cellular membranes, not only those of brain capillary endothelial cells.

SUMMARY OF THE INVENTION

The present invention pertains to a method for delivering a neuropharmaceutical agent across the blood brain barrier to the brain of a host. The method comprises administering to the host a ligand-neuropharmaceutical agent fusion protein wherein the ligand is reactive with a brain capillary endothelial cell receptor. The ligand of the fusion protein is an intact ligand to a brain capillary endothelial cell receptor or a receptor-binding fragment thereof. Alternatively, the ligand can be an antibody or immunoreactive fragment thereof that is reactive with a brain capillary endothelial cell receptor. The neuropharmaceutical agent of the fusion protein is a protein, polypeptide or peptide. The fusion protein is administered under conditions whereby binding of the ligand to a receptor on a brain capillary endothelial cell occurs and the neuropharmaceutical agent is transferred across the blood brain barrier in a pharmaceutically active form and in a therapeutically effective amount.

The present invention also pertains to a delivery system comprising a ligand-neuropharmaceutical agent fusion protein wherein the ligand is reactive with a brain capillary endothelial cell receptor. This delivery system transports the neuropharmaceutical agent across the blood brain barrier in a pharmaceutically active form when the fusion protein is administered in vivo. The present invention also pertains to the fusion proteins themselves which have both ligand binding and neuropharmaceutical characteristics.

Fusion proteins which include a brain capillary endothelial cell receptor ligand and an antibody, or immunoreactive fragment thereof, that is itself reactive with a brain capillary endothelial cell receptor are other aspects of the present invention. In these aspects, neuropharmaceutical agents can be conjugated to the fusion proteins by cleavable or non-cleavable linkers for transport of these agents across the blood brain barrier. Also pertaining to the present invention are a delivery system incorporating these fusion proteins and a method for delivering the neuropharmaceutical agent across the blood brain barrier in a pharmaceutically active form by administering to the host a fusion protein-neuropharmaceutical agent conjugate in a therapeutically effective amount.

Presently available means for delivering neuropharmaceutical agents to the brain are limited in that they are invasive. The delivery system of the present invention is non-invasive and can utilize readily available ligands reactive with brain capillary endothelial cell receptors as carriers for neuropharmaceutical agents. The delivery system is advantageous in that the ligands, when formed as part of a fusion protein with neuropharmaceutical agents, are capable of transporting the neuropharmaceutical agents across the blood brain barrier without being susceptible to premature release of the neuropharmaceutical agent prior to reaching the brain side of the blood brain barrier. The delivery system is similarly advantageous when the neuropharmaceutical agent is conjugated to the fusion protein by a nonclearable bond.

DESCRIPTION OF THE DRAWINGS

FIGS. 9A and 9B are the DNA sequence between the XhoI and EagI sites of clone CD51neg1, where the coding sequences for the CD5 Leader and IgG1 Exons 1, 2 and 3 are displayed in larger, bold characters (Seq.I.D.NO.8).

DETAILED DESCRIPTION

Figure 1:
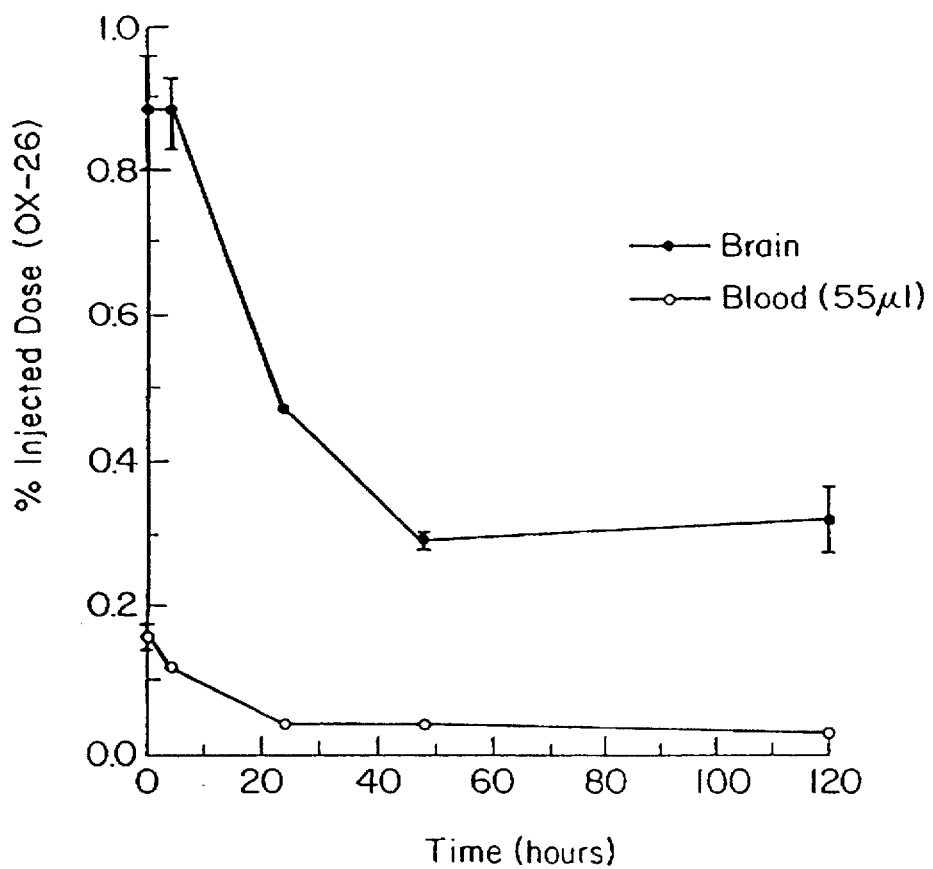
FIG. 1 is a graphic representation of rat brain uptake of $^{14}$C-labelled murine monoclonal antibody (OX-26) to rat transferrin receptor in rats where the percent injected dose of radiolabelled antibody per brain and per 55 µl of blood is plotted versus time post-injection.

The method for delivering a neuropharmaceutical agent across the blood brain barrier to the brain of a host comprises administering to the host a ligand-neuropharmaceutical agent fusion protein wherein the ligand is reactive with a receptor present on a brain capillary endothelial cell. The method is conducted under conditions whereby the ligand binds to the receptor on the brain capillary endothelial cell and the neuropharmaceutical agent is transferred across the blood brain barrier in a pharmaceutically active form and in a therapeutically effective amount.

The ligand-neuropharmaceutical agent fusion protein, which has both ligand binding and neuropharmaceutical characteristics, can be produced as a contiguous protein by using genetic engineering techniques. Gene constructs can be prepared comprising DNA encoding the ligand fused to DNA encoding the protein, polypeptide or peptide to be delivered across the blood brain barrier. The ligand coding sequence and the agent coding sequence are inserted in the expression vectors in a suitable manner for proper expression of the desired fusion protein. The gene fusion is expressed as a contiguous protein molecule containing both a ligand portion and a neuropharmaceutical agent portion. For example, sequences encoding neurotrophic agents such as NGF (nerve growth factor) or CNTF (ciliary neurotrophic factor) can be fused with the sequence encoding transferrin to create chimeric polypeptides that will be expressed and subsequently transported across the BBB via the transferrin receptor.

The genetic engineering techniques are often used to insert linker DNA sequences between the ligand and the neuropharmaceutical agent DNA encoding sequences. These linker DNA sequences can be expressed as part of the fusion protein. For example, specific segments of the constant region of an antibody, including the hinge region, can be inserted between the ligand and the neuropharmaceutical agent. These expressed insertions serve to separate the ligand from the neuropharmaceutical agent and may facilitate the proper folding of the expressed ligand or agent into its proper conformation. When the insertions are segments from the constant region of antibodies that are syngeneic to the host, they have the added advantage of having reduced immunogenicity when administered.

The host can be an animal susceptible to a neurological disorder (i.e., an animal having a brain). Examples of hosts include mammals such as humans, domestic animals (e.g., dog, cat, cow or horse), mice and rats.

The neuropharmaceutical agent can be an agent having a therapeutic or prophylactic effect on a neurological disorder or any condition which affects biological functioning of the central nervous system. Examples of neurological disorders include cancer (e.g. brain tumors), Acquired Immune Deficiency Syndrome (AIDS), stroke, epilepsy, Parkinson's disease, autoimmune diseases such as multiple sclerosis, neurodegenerative disease, trauma, depression, Alzheimer's disease, migraine, pain, or a seizure disorder. Classes of neuropharmaceutical agents which can be used in this invention include proteins and polypeptides used to treat or prevent a neurological disorder. Examples of proteins include growth factors (e.g. nerve growth factor (NGF)), ciliary neurotrophic factor (CNTF), brain-derived neurotrophic factor (BDNF), glial cell-line derived neurotrophic factor (GDNF), neurotrophins 3,4 and 5 (NT-3,4 and 5) or fibroblast growth factor (FGF), lymphokines or cytokines (e.g. interferon or interleukins (IL-2)) or antagonists thereof, CD4 and superoxide dismutase (including soluble portions thereof), dopamine decarboxylase and tricosanthin. Examples of polypeptides include somatostatin analogues and enkephalinase inhibitors.

The ligand of the fusion protein is any polypeptide or protein that is capable of binding with specificity to a receptor on brain capillary endothelial cells. These receptors are normally located on the luminal surfaces of these endothelial cells when they line the inner portion of the brain blood vessels. A particularly preferred ligand family is transferrin and any transferrin derivatives which retain transferrin receptor-binding activity.

Serum transferrin is a monomeric glycoprotein with a molecular weight of 80,000 daltons that binds iron in the circulation and transports it to the various tissues (Aisen et al. (1980) *Ann. Rev. Biochem.* 49: 357–393; MacGillivray et al. (1981) *J. Biol. Chem.* 258: 3543–3553). The uptake of iron by individual cells is mediated by the transferrin receptor, an integral membrane glycoprotein consisting of two identical 95,000 dalton subunits that are linked by a disulfide bond. The number of receptors on the surface of a cell appears to correlate with cellular proliferation, with the highest number being on actively growing cells and the lowest being on resting and terminally differentiated cells. Jeffries et al. (*Nature* 312, pp. 167–168 (November 1984)) used monoclonal antibodies to show that brain capillary endothelial cells have a high density of transferrin receptors on their cell surface.

Fusion proteins comprising ligands and neuropharmaceutical agents can also be prepared where the ligands are reactive with other receptors, besides the transferrin receptor, which can also mediate the endocytotic or transcytotic process of transporting macromolecules across the blood-brain barrier. These receptors are also on the cell surface of the endothelial cells which line brain vessels.

Among the receptor types are those that react with insulin-like growth factors 1 or 2 (IGF 1 or 2) or insulin and derivatives of these ligands which retain receptor-binding activity. The therapeutic agents which can be conjugated to the ligands include the above-mentioned proteins such as nerve growth factor, ciliary neurotrophic factor, brain-derived neurotrophic factor, superoxide dismutase, CD-4 or anti-amyloid antibody.

The term receptor is intended to encompass the entire receptor or ligand-binding portions thereof. These portions of the receptor particularly include those regions sufficient for specific binding of the ligand to occur.

Ligands which can bind with specificity to brain capillary endothelial cell receptors include antibodies or antibody fragments that can bind with these receptors. These antibodies or antibody fragments are as capable of binding to the brain capillary endothelial cell receptors as the nominal receptor ligands. Upon binding of the antibodies to the receptors, transferal of the antibody and any attached agent across the blood brain barrier occurs. The agent can be attached by any acceptable means for joining the antibody and agent such that the agent can be transferred across the blood brain barrier in a pharmaceutically active form. In preferred embodiments, the attached substance is a neuropharmaceutical agent and the antibody or antibody fragment forms a fusion protein with the agent. The antibody has replaced the nominal ligand, such as transferrin or receptor-binding derivatives of transferrin, in these embodiments.

In other embodiments, an antibody or antibody fragment, which is immunoreactive with a brain capillary endothelial cell receptor, and a second ligand, which is reactive with the same or a different receptor type on the brain capillary endothelial cells, are joined together to form a fusion protein. The second ligand can be a second antibody or, more preferably, a nominal ligand such as transferrin, IGFI, IGF2 or insulin. Conversely, the two ligands of the fusion protein can be two nominal ligands. These fusion proteins have the advantage of possessing the capacity of interacting twice as readily with brain capillary endothelial cell receptors than the fusion proteins of the present invention which have only one ligand. These fusion proteins can be linked by either genetic or chemical conjugation means to neuropharmaceutical agents for transferal of these agents across the blood brain barrier in a pharmaceutically active form.

When fusion proteins comprising an antibody and a second ligand are used, the range of neuropharmaceutical agents that can be transferred across the blood brain barrier is markedly increased. In addition to proteins and polypeptides, other substances that can be linked to the fusion proteins include antibiotics, adrenergic agents, anticonvulsants, nucleotide analogs, chemotherapeutic agents, anti-inflammatory agents and anti-trauma agents used to treat or prevent a disease of the brain or central nervous system (CNS). Examples of antibiotics include amphotericin B, gentamicin sulfate and pyrimethamine. Examples of adrenergic agents (including blockers) include dopamine and atenolol. Examples of chemotherapeutic agents include adriamycin, methotrexate, cyclophosphamide, etoposide and carboplatin. An example of an anticonvulsant which can be used is valproate and an anti-trauma agent which can be used is superoxide dismutase. Nucleotide analogs which can be used include azidothymidine (hereinafter AZT), dideoxyinosine (ddI) and dideoxycytodine (ddC). Examples of anti-inflammatory agents include tumor necrosis factor (TNF) and transforming growth factor (TGFβ).

The neuropharmaceutical agent can be linked to the antibody—second ligand fusion protein using chemical conjugation techniques. Generally, the link is made via an amine or a sulfhydryl group. The link can be a clearable link or non-cleavable link depending upon whether the neuropharmaceutical agent is more effective when released in its native form or whether the pharmaceutical activity of the agent can be maintained while linked to the fusion protein. The determination of whether to use a cleavable or non-cleavable linker can be made without undue experimentation by measuring the activity of the drug in both native and linked forms or for some drugs can be determined based on known activities of the drug in both the native and linked form.

For some cases involving the delivery of protein or peptide agents to the brain, release of the free protein or peptide may not be necessary if the biologically active portion of the protein or peptide agent is unaffected by its attachment to the fusion protein. As a result, antibody-protein or antibody-peptide conjugates can be constructed using noncleavable linkers.

Examples of non-cleavable linker systems which can be used in these embodiments include the carbodiimide (EDC), the sulfhydryl-maleimide, and the periodate systems. In the carbodiimide system, a water soluble carbodiimide reacts with carboxylic acid groups on proteins and activates the carboxyl group. The carboxyl group is coupled to an amino group of the second protein. The result of this reaction is a noncleavable amide bond between two proteins.

In the sulfhydryl-maleimide system, a sulfhydryl group is introduced onto an amine group of one of the proteins using a compound such as Traut's reagent. The other protein is reacted with an NHS ester (such as gamma-maleimidobutyric acid NHS ester (GMBS)) to form a maleimide derivative that is reactive with sulfhydryl groups. The two modified proteins are then reacted to form a covalent linkage that is noncleavable.

Periodate coupling requires the presence of oligosaccharide groups on either the fusion protein carrier or the protein to be delivered. If these groups are available on the protein to be delivered (as in the case of horseradish peroxidase (HRP)), an active aldehyde is formed on the protein to be delivered which can react with an amino group on the carrier. It is also possible to form active aldehyde groups from the carbohydrate groups present on antibody molecules. These groups can then be reacted with amino groups on the protein to be delivered generating a stable conjugate. Alternatively, the periodate oxidized antibody can be reacted with a hydrazide derivative of a protein to be delivered which will also yield a stable conjugate.

Cleavable linkers can be used to link neuropharmaceutical agents which are to be deposited in the brain or when a non-cleavable linker alters the activity of a neuropharmaceutical agent. Examples of cleavable linkers include the acid labile linkers described in copending patent application Ser. No. 07/308,960 filed Feb. 6, 1989, the contents of which are hereby incorporated by reference. Acid labile linkers include disulfides such as N-succinimidyl-3-(2-pyridyldithio) propionate (SPDP; Pharmacia), cis-aconitic acid, cis-carboxylic alkadienes, cis-carboxylic alkatrienes, and poly-maleic anhydrides. Other cleavable linkers are linkers capable of attaching to primary alcohol groups. Examples of neuropharmaceutical agents which can be linked via a cleavable link include AZT, ddI, ddC, adriamycin, amphotericin B, pyrimethamine, valproate, methotrexate, cyclophosphamide, carboplatin and superoxide dismutase. The nonclearable linkers used generally to link proteins to the antibody can also be used to link other neuropharmaceutical agents to the antibody.

SPDP is a heterobifunctional crosslinking reagent that introduces thiol-reactive groups into either the monoclonal antibody or the neuropharmaceutical agent. The thiol-reactive group reacts with a free sulfhydryl group forming a disulfide bond.

In addition to covalent bonding, conjugates can be formed employing non-covalent bonds, such as those formed with bifunctional antibodies, ionic bonds, hydrogen bonds, hydrophobic interactions, etc. The important consideration is that the conjugate bond be strong enough to result in passage of the conjugate through the blood-brain barrier.

Antibodies which can be used within this invention are reactive with a receptor on a brain capillary endothelial cell. The term antibody is intended to encompass both polyclonal and monoclonal antibodies. The preferred antibody is a monoclonal antibody reactive with a brain capillary endothelial cell receptor such as a transferrin receptor. The term antibody is also intended to encompass mixtures of more than one antibody reactive with a transferrin receptor (e.g., a cocktail of different types of monoclonal antibodies reactive with a transferrin receptor), each of which is joined to a neuropharmaceutical agent or another ligand to form a fusion protein. The term antibody is further intended to encompass whole antibodies, biologically functional fragments thereof, and chimeric antibodies comprising portions from more than one species, bifunctional antibodies, etc. Biologically functional antibody The chimeric antibodies can comprise portions derived from two different species (e.g., human constant region and murine variable or binding region). The portions derived from two different species can be joined together chemically by conventional techniques or can be prepared as fusion proteins using genetic engineering techniques. In addition, DNA encoding the proteins of both the light chain and heavy chain portions of the chimeric antibody can be expressed together as fusion proteins.

Such chimeric antibodies can readily be adapted to being part of the fusion proteins of this invention. The DNA which contains the variable region coding sequence can be fused to DNA which contains the neuropharmaceutical agent coding sequence for subsequent expression as a fusion protein. Likewise, the DNA which contains the variable region coding sequence can be fused to DNA which contains the coding sequence of a second ligand, if such an expressed fusion protein is desired. The chimeric antibodies comprising constant and variable region portions from two different species can easily be converted to fusion proteins of this invention by inserting DNA encoding a neuropharmaceutical agent or DNA encoding another ligand after a specific portion of constant region encoding DNA. The subsequently expressed fusion protein will then contain the variable region from one species, a desired portion of the constant region from another species and a second ligand or the agent to be transferred across the blood brain barrier.

Monoclonal antibodies reactive with at least a portion of the transferrin receptor can be obtained (e.g., OX-26, B3/25 (Omary et al. (1980) *Nature* 286: 888-891), T56/14 (Gatter et al. (1983) *J. Clin. Path.* 36: 539-545; Jefferies et al. *Immunology* (1985) 54: 333-341), OKT-9 (Sutherland et al. (1981) *Proc. Natl. Acad. Sci.* USA 78: 4515-4519), L5.1 (Rovera, C. (1982) *Blood* 59: 671-678), 5E-9 (Haynes et al. (1981) *J. Immunol.* 127: 347-351), RI7 217 (Trowbridge et al. *Proc. Natl. Acad. Sci.* USA 78: 3039 (1981) and T58/30 (Omary et al. cited supra) or can be produced using somatic cell hybridization techniques (Kohler and Milstein (1975) *Nature* 256: 495-497) or by other techniques. In a typical hybridization procedure, a crude or purified protein or peptide comprising at least a portion of the transferrin receptor can be used as the immunogen. An animal is vaccinated with the immunogen to obtain anti-transferrin receptor antibody-producing spleen cells. The species of animal immunized will vary depending on the species of monoclonal antibody desired. An antibody-producing cell is fused with an immortalizing cell (e.g. myeloma cell) to create a hybridoma capable of secreting anti-transferrin receptor antibodies. The unfused residual antibody-producing cells and immortalizing cells are eliminated. Hybridomas producing the anti-transferrin receptor antibodies are selected using conventional techniques and the selected anti-transferrin receptor antibody producing hybridomas are cloned and cultured. Similar somatic cell hybridization techniques can be used to produce hybridomas that secrete monoclonal antibodies immunoreactive with other brain capillary endothelial cell receptors.

Polyclonal antibodies can be prepared by immunizing an animal with a crude or purified protein or peptide comprising at least a portion of a transferrin receptor or of another brain capillary endothelial cell receptor. The animal is maintained under conditions whereby antibodies reactive with a transferrin receptor are produced. Blood is collected from the animal upon reaching a desired titer of antibodies. The serum containing the polyclonal antibodies (antisera) is separated from the other blood components. The polyclonal antibody-containing serum can optionally be further separated into fractions of particular types of antibodies (e.g. IgG, IgM).

The ligand-neuropharmaceutical agent fusion proteins or conjugates can be administered orally, by subcutaneous or other injection, intravenously, intra-arterially, intramuscularly, parenterally, transdermally, nasally or rectally. The form and concentration in which the conjugate is administered (e.g., capsule, tablet, solution, emulsion) will depend at least in part on the route by which it is administered.

A therapeutically effective amount of a ligand-neuropharmaceutical agent fusion protein or conjugate is that amount necessary to significantly reduce or eliminate symptoms associated with a particular neurological disorder. The therapeutically effective amount will be determined on an individual basis and will be based, at least in part, on consideration of the individuals's size, the severity of symptoms to be treated, the result sought, the specific ligand, etc. Thus, the therapeutically effective amount can be determined by one of ordinary skill in the art employing such factors and using no more than routine experimentation.

The present invention will be illustrated by the following examples:

EXAMPLE 1

In Vitro Binding of Murine Monoclonal Antibodies to Human Brain Endothelial Cells Two murine monoclonal antibodies, B3/25 and T58/30, described by Trowbridge (U.S. Pat. No. 4,434,156 issued Feb. 28, 1984, and *Nature* 294, pp. 171–173 (1981)), the contents of both are hereby incorporated by reference, which recognize the human transferrin receptor were tested for their ability to bind to human brain capillary endothelial cells. Hybridoma cell lines which produce B3/25 and T58/30 antibodies were obtained from the American Type Culture Collection (ATCC) in Rockville, Md., and grown in DMEM medium supplemented with 2.0 mM glutamine, 10.0 mM HEPES (pH 7.2), 100 µM non-essential amino acids and 10% heat-inactivated fetal calf serum. The hybridoma cultures were scaled-up in 225 cm$^2$ T-flasks for the production of milligram quantities of IgG antibody. The hybridoma supernatants were concentrated 50× using vacuum dialysis and applied to a protein-A sepharose column using the BioRad MAPS buffer system. Purified antibody was eluted from the column, dialyzed against 0.1M sodium phosphate (pH 8.0), concentrated and stored in aliquots at −20° C.

Primary cultures of human brain endothelial cells were grown in flat-bottom 96-well plates until five days post-confluency. The cells were then fixed using 3.0% buffered formalin and the plate blocked with 1.0% bovine serum albumin (BSA) in Dulbecco's phosphate buffered saline (DPBS). Aliquots (100 µl) of the B3/25 or T58/30 antibodies, either in the form of culture supernatants or purified protein, were then added to the wells (antibody concentrations were in the range of 1–50 µg/ml). Antibody which had specifically bound to the fixed cells was detected using a biotin-labeled polyclonal goat-anti-mouse IgG antisera followed by a biotinylated horseradish peroxidase (HRP)/avidin mixture (Avidin Biotin Complex technique). Positive wells were determined using a Titertek Multiscan Enzyme Linked Immunosorbent Assay (ELISA) plate reader. The results showed that both antibodies bind to human brain capillary endothelial cells with the T58/30 antibody exhibiting a higher level of binding.

These same antibodies were also tested for binding to human brain capillaries using sections of human brain tissue that were fresh frozen (without fixation), sectioned on a cryostat (section thickness was 5–20 µm), placed on glass slides and fixed in acetone (10 minutes at room temperature). These sections were then stored at −20° C. prior to use.

The slides containing the human brain sections were allowed to come to room temperature prior to use. The sections were then rehydrated in DPBS and incubated in methanol containing 0.3% $H_2O_2$ to block endogenous peroxidate activity. The sections were blocked for fifteen minutes in a solution containing 0.2% non-fat dry milk and 0.2% methylmannopyranoside. B3/25 and T58/30 antibodies, purified as discussed above, were applied to the sections at a concentration of 5–50 µg/ml and incubated at room temperature for one to two hours. Antibody that specifically bound to the tissue was detected using the Avidin-Biotin Complex (ABC) technique as described above for the ELISA assay. Staining of capillaries in the human brain sections was observed with both the B3/25 and T58/30 antibodies. The T58/30 antibody also displayed some binding to the white matter of the brain cortex.

EXAMPLE 2

In-Vitro Binding of Murine Monoclonal Antibody OX-26 to Rat Transferrin Receptor The OX-26 murine antibody, which recognizes the rat transferrin receptor, has been shown in vivo to bind to brain capillary endothelial cells (Jeffries et al., cited supra). The murine hybridoma line which produces the OX-26 murine antibody was obtained and the hybridoma cell line was grown in RPMI 1640 medium supplemented with 2.0 mM glutamine and 10% heat-inactivated fetal calf serum. The OX-26 antibody was purified using the affinity chromatography technique described in Example 1.

The purified antibody was tested in vitro as described for the anti-human transferrin receptor antibodies in Example 1 to determine whether it would bind to brain capillaries in fresh frozen, acetone-fixed rat brain sections. The results showed that the OX-26 anti-transferrin receptor antibody did bind to capillaries in rat brain sections in vitro.

EXAMPLE 3

In-Vivo Binding of OX-26 Murine Monoclonal Antibody to Rat Transferrin Receptor

Dose Range

The anti-rat transferrin receptor antibody OX-26 was tested in vivo by injecting purified antibody (purification as described in Example 1) into female Sprague-Dawley rats (100–150 gm) via the tail vein. Prior to injection, the rats were anesthetized with halothane. The samples, ranging from 2.0 mg to 0.05 mg of antibody/rat were injected into the tail vein in 400 µl aliquots. All doses were tested in duplicate animals. One hour post-injection, the animals were sacrificed and perfused through the heart with DPBS to clear the blood from the organs. Immediately after the perfusion was completed, the brain was removed and quick frozen in liquid nitrogen. The frozen brain was then sectioned (30–50 µm) on a cryostat and the sections placed on glass microscope slides. The brain sections were air dried at room temperature one to two hours before fixation in acetone (10 minutes at room temperature). After this treatment the sections could be stored at −20° C.

The OX-26 antibody was localized in the brain sections using immunohistochemistry as described above for the in vitro experiments in Example 1. The addition of the primary antibody was unnecessary in that it is present in the brain sections. The results indicated that the OX-26 antibody binds to rat brain capillary endothelial cells and that doses of as little as 50 µg result in detectable levels of antibody in the brain using the methods described herein. Doses above 0.5 mg did not appear to show significantly more antibody binding to the endothelial cells, suggesting that the sites for antibody binding may be saturated. No specific binding to capillary endothelium was detected in the liver, kidney, heart, spleen or lung.

A non-specific antibody of the same subclass as OX-26 (IgG 2a) was also tested in vivo to show that the binding of OX-26 to rat brain endothelial cells that has been observed is specific to the OX-26 antibody. 0.5 mg of the control antibody was injected per rat as described above. The results indicate that the staining pattern observed with the OX-26 antibody is specific to that antibody.

Time Course

After establishing that the OX-26 antibody is detectable in the rat brain capillaries after in vivo administration, the time frame in which this binding occurred was determined. Using 0.5 mg of purified OX-26 antibody as the standard dose, brain sections taken from animals sacrificed 5 minutes, 15 minutes, 1 hour, 2 hours, 4 hours, 8 hours and 24 hours post-injection were examined for the presence of OX-26 antibody. All doses were administered in 400 ul aliquots and each time point was tested in duplicate animals. Samples were injected and the rats were processed at the various times postinjection as described above in the dose range section.

The results showed that the OX-26 antibody can be detected in or on the rat brain capillary endothelial cells as early as five minutes and as late as 24 hours post-injection. At 4 and 8 hours post-injection, the staining pattern of the antibody is very punctate suggesting that the antibody has accumulated in vesicular compartments either in endothelial or perivascular cells.

EXAMPLE 4

The Use of a Conjugate of OX-26 Murine Monoclonal Antibody for Transferring Horseradish Peroxidase Across the Blood Brain Barrier Horseradish Peroxidase (HRP; 40 kD) was chosen as a compound to be delivered to the brain because it is similar in size to several therapeutic agents and it can be easily detected in the brain using an enzymatic assay. HRP was conjugated to the OX-26 antibody using a non-cleavable periodate linkage and the ability of the antibody to function as a carrier of compounds to the brain was examined. The antibody conjugate was tested in vivo to determine if the antibody could deliver HRP to the brain.

The antibody (10 mg) was first dialyzed overnight against 0.01M sodium bicarbonate (pH 9.0). The HRP (10 mg) was dissolved in 2.5 ml deionized water, 0.1M sodium periodate (160 µl) was added and the mixture was incubated for five minutes at room temperature. Ethylene glycol (250 µl) was added to the HRP solution followed by an additional five minute incubation. This solution was then dialyzed overnight against 1.0 mM sodium acetate buffer (pH 4.4). To the dialyzed OX-26 antibody (2.0 ml, 5.08 mg/ml) was added 200 µl of 1.0M sodium bicarbonate buffer, pH 9.5 and 1.25 ml of the dialyzed HRP solution. This mixture was incubated in the dark for two hours followed by the addition of 100 µl of 10 mg/ml sodium borohydride. The resulting mixture was incubated for two additional hours in the dark at 4° C. The protein was precipitated from the solution by the addition of an equal volume of saturated ammonium sulfate and resuspended in a minimal volume of water. Free antibody was removed from the mixture by chromatography on a concanavalin A-sepharose column (a column which binds HRP and the HRP-antibody conjugate and allows the free antibody to pass through). The free HRP was removed by chromatography on a protein A-sepharose column which retains the antibody-HRP conjugate. The final product had an E/antibody ratio of 4/1.

A time course experiment identical to that described in Example 3 was performed using the antibody-HRP conjugate. The antibody-HRP conjugate (0.5 mg) was injected in a 400 µl aliquot/rat. The animals were sacrificed at the various times post-injection and the brains processed as described above in Example 3. The antibody HRP conjugate was localized in the brain either by staining for antibody immunohistochemically as described in Example 1 or by directly staining the brain sections for the presence of HRP. To detect HRP, the slides were first allowed to come to room temperature before incubating in methanol for thirty minutes. The brain sections were then washed in DPBS and reacted with 3,3'-diamino benzidine (DAB), the substrate for HRP. The results showed that the OX-26 antibody HRP conjugate binds to rat brain capillary endothelial cells in a manner identical to that of the unconjugated antibody. The punctate staining 4–8 hours after injection which was seen with the antibody alone is also seen with the antibody conjugate, suggesting that the conjugate can also be going into the pericytes on the abluminal side of the blood brain barrier. Taken together, these results indicate that the OX-26 antibody can deliver a protein molecule of at least 40 KD to the brain.

EXAMPLE 5

The In-Vivo Delivery of Adriamycin to the Brain by Murine Monoclonal Antibody OX-26

A non-cleavable linker system similar to that used in Example 4, was used to couple the chemotherapeutic drug adriamycin to the OX-26 antibody. The availability of antibodies that can detect adriamycin as well as the system previously described in Example 1 for detecting the antibody carrier allowed the use of immunohistochemical techniques for monitoring the localization of the antibody carrier as well as the delivery of adriamycin to the brain.

To conjugate adriamycin to the antibody, the drug (10 mg in 0.5 ml DPBS) was oxidized by the addition of 200 µl of 0.1M sodium periodate. This mixture was incubated for one hour at room temperature in the dark. The reaction was quenched by the addition of 200 µl of ethylene glycol followed by a five minute incubation. The OX-26 antibody (5.0 mg in 0.5 ml of carbonate buffer (pH 9.5)) was added to the oxidized adriamycin and incubated at room temperature for one hour. Sodium borohydride (100 µl of 10 mg/ml) was added and the mixture was incubated for an additional two hours at room temperature. The free adriamycin was separated from the OX-26 antibody-adriamycin conjugate by chromatography on a PD-10 column. The adriamycin/OX-26 antibody ratio within the conjugate was 2/1 for this particular batch of conjugate.

The effectiveness of the OX-26 antibody as a carrier for delivering adriamycin to the brain was determined by administering 0.5 mg of the antibody-adriamycin conjugate in a 400 µl aliquot per rat by injection via the tail vein. One hour post-injection, the rat was sacrificed and the brain processed as described in Example 1. All injections were performed in duplicate. As a control, 400 µg of free adriamycin in a 400 µl aliquot was also injected into a rat. Immunohistochemistry was used to detect both the carrier OX-26 antibody and the adriamycin in the rat brain sections. In the case of adriamycin, polyclonal rabbit anti-adriamycin antisera was applied to the sections followed by a biotinylated goat anti-rabbit IgG antisera. This was then followed by the addition of a biotinylated HRP/avidin mixture and enzymatic detection of HRP.

The results indicate that both the OX-26 antibody and the conjugated adriamycin localized to the rat brain capillary endothelial cells after in vivo administration. There is no evidence that free adriamycin binds to brain capillary endothelial cells or enters the brain.

An adriamycin-OX-26 conjugate coupled via a carbodiimide linkage was also synthesized (drug/antibody ratio of 10/1) and tested in vivo. The results of this experiment were essentially identical to that obtained with the periodate-linked antibody-drug conjugate. In both cases, staining for the antibody carrier was quite strong and was visualized in the capillaries in all areas of the brain. This staining was evenly distributed along the capillaries. Staining for adriamycin was less intense but again was seen in capillaries throughout the brain. Some punctate staining was observed which suggests accumulation in pericytes which lie on the brain side of the blood-brain barrier.

EXAMPLE 6

In Vivo Delivery of Methotrexate to the Brain by Murine Monoclonal Antibody OX-26

A noncleavable carbodiimide linkage was used to couple methotrexate to the OX-26 murine monoclonal antibody. A system analogous to that described in Example 5 was used to monitor the delivery of both the methotrexate and the carrier antibody to the brain capillary endothelial cells.

Methotrexate was coupled to murine monoclonal antibody OX-26 via its active ester. Briefly, 81 mg (0.178 mM) of methotrexate (Aldrich) was stirred with 21 mg (0.182 mM) of N-hydroxysuccinimide (Aldrich) in 3 ml of dimethylformamide (DMF) at 4° C. Ethyl-3-dimethylaminopropyl-carbodiimide (180 mg,EDC;O.0.52 mM) was added to this solution and the reaction mixture was stirred overnight. The crude ester was purified from the reaction by-products by flash chromatography over silica gel 60 (Merck) using a solution of 10% methanol in chloroform as an eluant. The purified active ester fractions were pooled and concentrated to dryness. The ester was dissolved in 1 ml of DMF and stored at −20° C. until use. 50 mg (50%) of active ester was recovered as determined by $A_{372}(\epsilon_{372}=7200)$.

A solution of OX-26 containing 2.1 mg (14 nmoles) of antibody in 0.9 ml of 0.1M phosphate (pH 8.0) was thawed to 4° C. To this stirred antibody solution was added 1.4 µl (140 nmoles) of the active ester prepared as described above. After 16 hours at 4° C., the mixture was chromatographed over Sephadex PD-10 column (Pharmacia) using phosphate buffered saline (PBS) to separate conjugate from free drug. The fractions containing the antibody-methotrexate conjugate were pooled. Antibody and drug concentration were determined spectrophotometrically as described by Endo et al. (*Cancer Research* (1988) 48: 3330–3335). The final conjugate contained 7 methotrexates/antibody.

The ability of the OX-26 monoclonal antibody to deliver methotrexate to the rat brain capillary endothelial cells was tested in vivo by injecting 0.2 mg of conjugate (in 400 µl ) into each of two rats via the tail vein. The animals were sacrificed one hour post-injection and the brains processed for immunohistochemistry as described in Example 1. To detect methotrexate in the brain, a rabbit antisera raised against methotrexate was used as the primary antibody. A biotinylated goat-anti-rabbit antisera in conjunction with a mixture of biotinylated HRP and avidin was then used to visualize methotrexate in the rat brain. The carrier antibody was detected as described previously.

The results of these experiments indicate that methotrexate in the form of a conjugate with OX-26 does accumulate along or in the capillary endothelial cells of the brain. The staining observed for methotrexate is comparable in intensity to that seen for the carrier. The staining appears to be in all areas of the brain and is evenly distributed along the capillaries.

EXAMPLE 7

Antibody Derivatives

The Fc portion of the OX-26 murine monoclonal antibody was removed to determine whether this would alter its localization to or uptake by the rat brain capillary endothelial cells. F(ab)$_2$ fragments of OX-26 were produced from intact IgG's via digestion with pepsin. A kit available from Pierce Chemical Co. contains the reagents and protocols for cleaving the antibody to obtain the fragments The F(ab')$_2$ fragment (0.2 mg doses) in 400 µl aliquots were injected into rats via the tail vein. A time course experiment identical to that done with the intact antibody (Example 2) was then performed. F(ab')$_2$ fragment was detected immunohistochemically using a goat anti-mouse F(ab')$_2$ antisera followed by a biotinylated rabbit anti-goat IgG antisera. A biotinylated HRP/avidin mixture was added and the antibody complex was visualized using an HRP enzymatic assay. The results indicate that the F(ab)$_2$ fragment of the OX-26 antibody binds to the capillary endothelial cells of the rat brain.

EXAMPLE 8

Measurement of OX-26 in Brain Tissue

To quantitate the amount of OX-26 which accumulates in the brain, radioactively-labelled antibody was injected into rats via the tail vein. Antibodies were labelled with either $^{14}$C-acetic anhydride or $^3$H-succinimidyl propionate essentially as described in Kummer, U., *Methods in Enzymology*, 121: 670–678 (1986), Mondelaro, R. C., and Rueckert, R. R., *J. of Biological Chemistry*, 250: 1413–1421 (1975), hereby incorporated by reference. For all experiments, the radiolabelled compounds were injected as a 400 µl bolus into the tail vein of female Sprague-Dawley rats (100–125 gms) under Halothane anesthesia and the animals were sacrificed at the appropriate time post-injection using a lethal dose of anesthetic. A $^3$H-labelled IgG2a control antibody was co-injected with the $^{14}$C-labelled OX-26 to serve as a control for non-specific radioactivity in the brain due to residual blood. At the appropriate time post-injection, animals were sacrificed and the brains were removed immediately and homogenized in 5 ml of 0.5% sodium dodecylsulfate using an Omni-mixer. An aliquot of the homogenate was incubated overnight with 2 ml of Soluene 350 tissue solubilizer prior to liquid scintillation counting. All data were collected as disintegrations per minute (dpm). Blood samples were centrifuged to pellet red blood cells (which do not display significant binding of radiolabelled materials) and the radioactivity in an aliquot of serum determined using liquid scintillation counting.

The amount of antibody associated with the brain was determined at various times post-injection to examine the pharmacokinetics of brain uptake. In addition, the amount of labelled antibody in the blood was measured so that the rate of clearance from the bloodstream could be determined. This information was also used to calculate the amount of radioactivity in the brain due to blood contamination, which was then subtracted from the total to give the amount of antibody that is specifically associated with the brain.

A peak level of $^{14}$C-labelled OX-26 corresponding to approximately 0.9% of the injected dose was reached in the brain between 1 and 4 hours post-injection as illustrated in FIG. 1 (with the values shown as means plus or minus standard error of the mean (SEM) and N=3 rats per time point). The amount of radioactivity associated with the brain decreased steadily from 4 to 48 hours post-injection, at which point it leveled off at approximately 0.3% of the injected dose. The accumulation of OX-26 in the brain was significantly reduced by the addition of unlabelled monoclonal antibody (0.5 or 2.0 mg in the bolus injection). As an additional control, a $^3$H-IgG2a control antibody was co-injected with the $^{14}$C-OX-26. The control antibody did not accumulate in the brain and represented the blood contamination of the brain.

In contrast to the levels in the brain, the blood level of OX-26 dropped quite dramatically immediately after injection such that by 1 hour post-injection, the percent of injected dose in 55 μl of blood (the volume of blood associated with the brain) was approximately 0.16% as illustrated in FIG. 1. This corresponds to a value of approximately 20% of the injected dose in the total blood volume of the rat. Extraction of total IgG from serum followed by polyacrylamide gel electrophoresis (PAGE) and autoradiography did not reveal detectable levels of OX-26 degradation indicating that the antibody remains intact in the blood as long as 48 hours after injection.

EXAMPLE 9

Distribution of OX-26 in Brain Parenchyma and Capillaries

To demonstrate that anti-transferrin receptor antibody accumulates in the brain parenchyma, homogenates of brains taken from animals injected with labelled OX-26 were depleted of capillaries by centrifugation through dextran to yield a brain tissue supernatant and a capillary pellet. Capillary depletion experiments followed the procedure of Triguero, et al., *J. of Neurochemistry*, 54: 1882–1888 (1990), hereby incorporated by reference. As for the brain uptake experiments of Example 8, the radiolabelled compounds were injected as a 400 μl bolus into the tail vein of female Sprague-Dawley rats (100–125 gm) under Halothane anesthesia and the animals were sacrificed at the appropriate time post-injection using a lethal dose of anesthetic. A $^3$H-labelled IgG 2a control antibody was co-injected with the $^{14}$C-labelled OX-26 to serve as a control for non-specific radioactivity in the brain due to residual blood. After sacrifice, the brains were removed and kept on ice. After an initial mincing, the brains were homogenized by hand (8–10 strokes) in 3.5 ml of ice cold physiologic buffer (100 mM NaCl, 4.7 mM KCl, 2.5 mM $CaCl_2$, 1.2 mM $KH_2PO_4$, 1.2 mM $MgSO_4$, 14.5 mM HEPES, 10 mM D-glucose, pH 7.4). Four ml of 26% dextran solution in buffer was added and homogenization was continued (3 strokes). After removing an aliquot of the homogenate, the remainder was spun at 7200 rpm in a swinging bucket rotor. The resulting supernatant was carefully removed from the capillary pellet. The entire capillary pellet and aliquots of the homogenate and supernatant were incubated overnight with 2 ml of Soluene 350 prior to liquid scintillation counting. This method removes greater than 90% of the vasculature from the brain homogenate (Triguero et al., cited supra).

Figure 2:
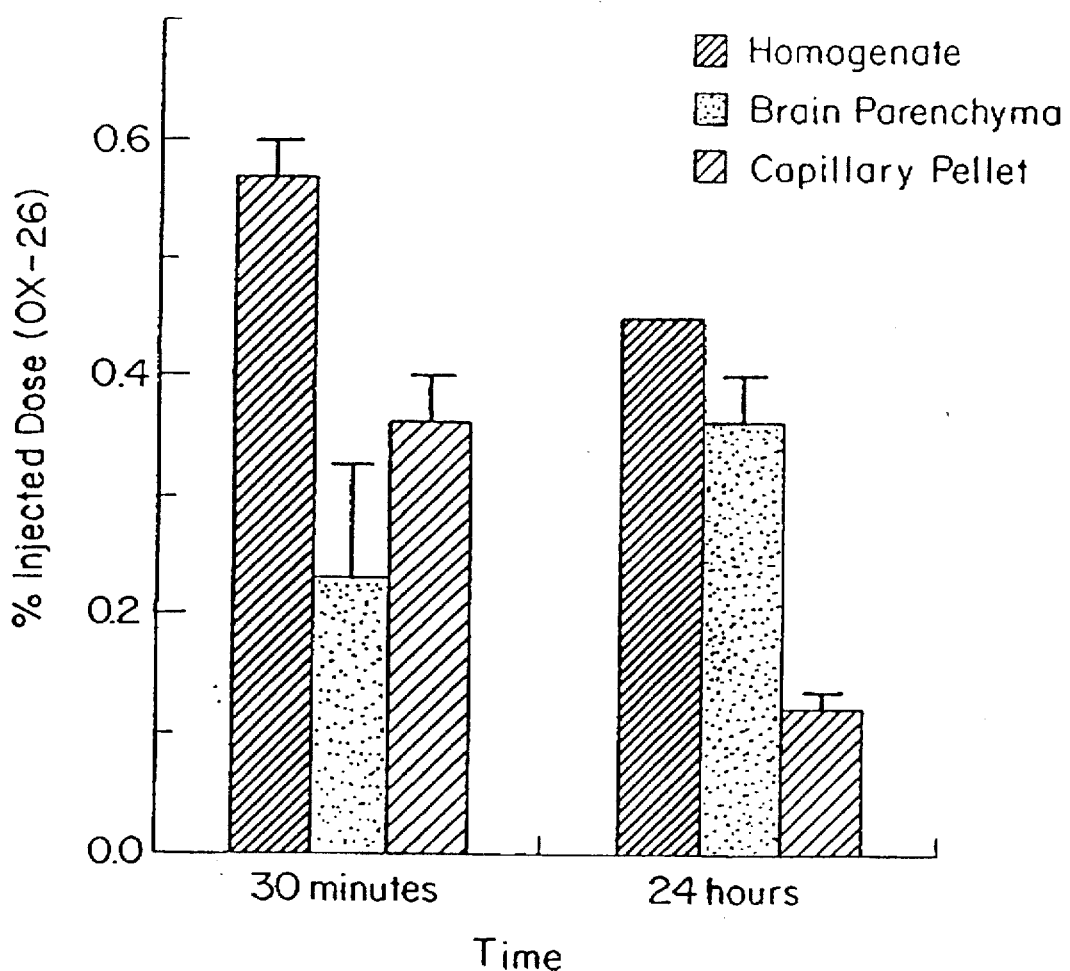
FIG. 2 is a histogram illustrating time dependent changes in the disposition of radiolabelled OX-26 between brain parenchyma and vasculature.

A comparison of the relative amounts of radioactivity in the different brain fractions as a function of time indicates whether transcytosis of the labelled antibody has occurred. The amount of OX-26 in total brain homogenate, the brain parenchyma fraction and the brain capillary fraction at an early time (30 minutes) and a later time (24 hours) post-injection is illustrated in FIG. 2. The values in FIG. 2 are shown as means±SEM with N=3 rats per time point. At the 30 minute time point, more of the radiolabelled antibody is associated with the capillary fraction than with the brain parenchyma fraction (0.36% of the injected dose (%ID) and 0.23% ID, respectively). By 24 hours post-injection, the distribution is reversed and the majority of the radioactivity (0.36% ID) is in the parenchymal fraction as compared to the capillary fraction (0.12% ID). The redistribution of the radiolabelled OX-26 from the capillary fraction to the parenchyma fraction is consistent with the time dependent migration of the anti-transferrin receptor antibody across the blood-brain barrier.

EXAMPLE 10

Biodistribution and Brain Uptake of Anti-Human Transferrin Receptor Antibodies in Cynomolgous Monkeys A collection of 32 murine monoclonal antibodies which recognize various epitopes on the human transferrin receptor were examined for reactivity with brain capillary endothelial cells in sections from human, monkey (cynomolgous), rat and rabbit brain samples by the immunohistochemical methods described in Example 1. These antibodies were obtained from Dr. Ian Trowbridge of the Salk Institute, LaJolla, Calif. All 32 antibodies displayed some reactivity with human brain endothelial cells. Two antibodies reacted very weakly with rabbit brain capillaries and none reacted with rat. While 21 of the antibodies reacted with monkey brain capillaries, only 2 displayed strong reactivity comparable to that seen with human brain capillaries. These 2 antibodies are herewithin referred to as 128.1 and Z35.2.

Figure 3:
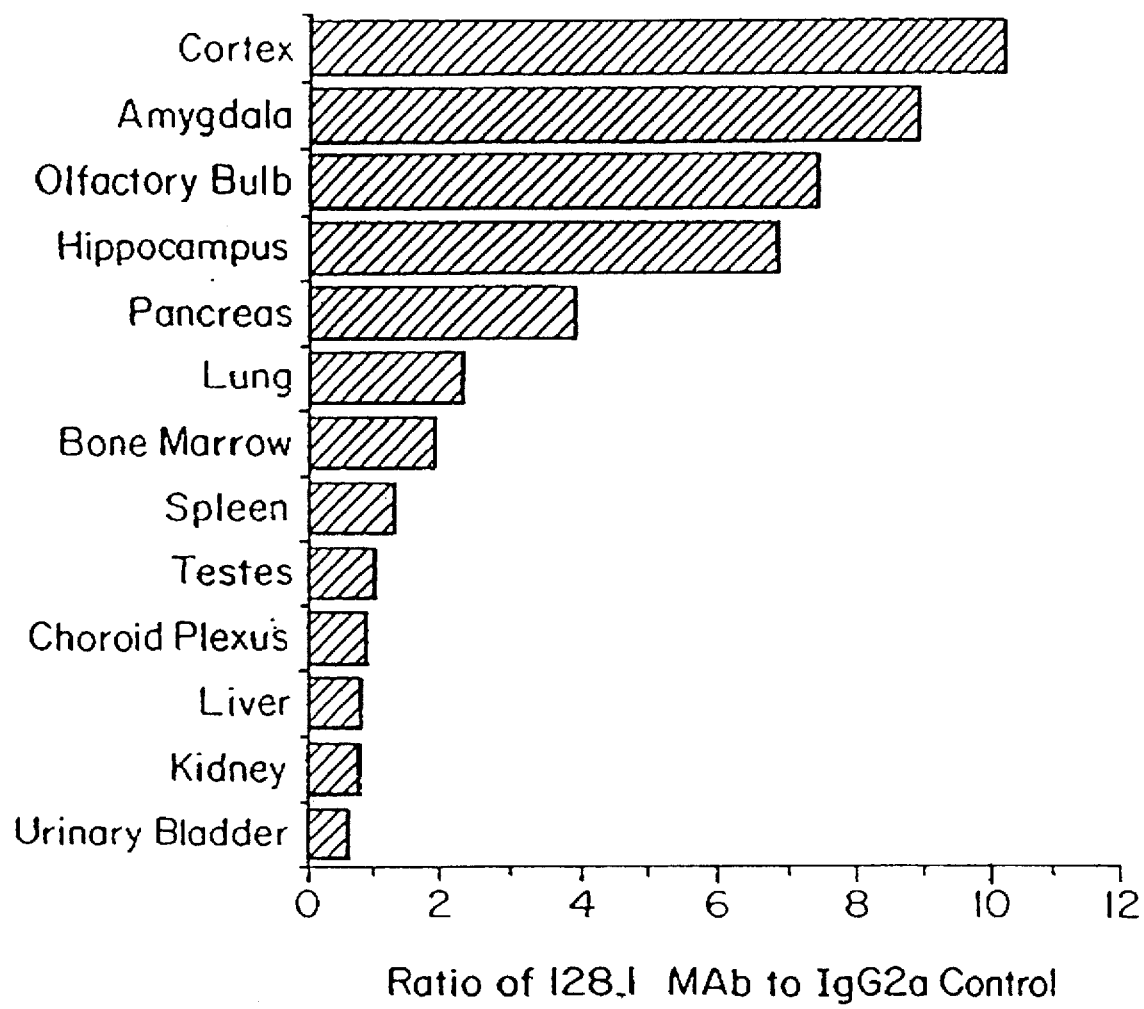
FIG. 3 is a histogram illustrating the biodistribution of antibody 128.1 and control IgG in a cynomolgus monkey.

These antibodies were used to determine the tissue distribution and blood clearance of the $^{14}$C-labelled anti-human transferrin receptor antibodies 128.1 and Z35.2 in 2 male cynomolgous monkeys. 128.1 or Z35.2 was administered concurrently with a $^3$H-labelled control IgG to one of the monkeys with an intravenous catheter. During the course of the study, blood samples were collected to determine the clearance of the antibodies from the circulation. At 24 hours post-injection, the animals were euthanized and selected organs and representative tissues were collected for the determination of isotope distribution and clearance by combustion. In addition, samples from different regions of the brain were processed as described for the capillary depletion experiments in Example 9 to determine whether the antibodies had crossed the blood-brain barrier. The results of the capillary depletion experiments were performed on samples from the cortex, frontal cortex, cerebellum and striatum. All samples had greater than 90% of the 128.1 or Z35.2 in the brain parenchyma, suggesting that the antibodies crossed the blood-brain barrier. The levels of the control antibody in the same samples were from 5 to 10-fold lower. Using the average brain homogenate value for dpm/G tissue, the percent injected dose of 128.1 in the whole brain is approximately 0.2–0.3%. This compares to a value of 0.3–0.5% for OX-26 in the rat at 24 hours post-injection. A comparison of the ratios of 128.1 to the control antibody for various organs is illustrated in FIG. 3. Similar results were obtained for Z35.2. These results suggest that 128.1 is preferentially taken up by the brain as compared to control antibody. For the majority of organs and tissues tested, the ratio of 128.1 to control is less than 2.

EXAMPLE 11

Construction of a NGF-IgG3 Hinge-Transferrin Fusion eerie, Expression of the NGF-IgG3 Hinge-Transferrin Fusion Gene as a Fusion Protein and Assay of the Fusion Protein Constituents A fusion protein comprised of human NGF and human transferrin was constructed using the human IgG3 hinge region as a linker between the NGF and transferrin polypeptides. The IgG3 hinge region, which is about 60 amino acids long and includes a number of cysteine residues, was chosen as a connector between the NGF and transferrin polypeptides. The potential for disulfide formation within the immunoglobulin hinge region was envisioned as increasing the probability of allowing the dimerization of the NGF polypeptides into a more native NGF configuration.

Preparation of a Bacterial Vector for Insertion of the NGF Gene

Bacterial plasmid pAT3442 (FIG. 4) was used as the starting plasmid for construction of the NGF-hinge-transferrin gene fusion. It contained human genomic DNA encoding the IgG3 CH1 (constant region 1 of the heavy chain) and hinge region and the human transferrin cDNA. This plasmid was constructed by the following procedure.

Bacterial plasmid pAT3442 was derived from vector pAT153 ("Practical Guide to Molecular Cloning", 1984, Bernard Perbal, John Wiley Publisher). pAT153 was first modified to remove the EcoRI site by cleavage of this vector with EcoRI, filling in of the 5' overhang regions with the use of DNA polymerase, and religation. This derivative was designated pAT153.7.

A SalI-BamHI fragment containing the sequence coding for human IgG3 constant region and the hinge region with its associated introns was isolated from phage lambda libraries as described in Dangl, J. L., (1986 Dissertation, Stanford University, Stanford, Calif.). A large portion of the untranslated region was eliminated from the 3' end of the IgG3 gene by cleavage with PvuII (which cleaves multiple times within this region) and religation. This fragment was further modified by site directed mutagenesis to contain a PvuII site at the 5' end of the CH2 region; cleavage with SmaI and introduction of an EcoRI linker resulted in the SmaI site in the CH3 region being joined to the SmaI site 0.6 kb upstream of the BamHI site with an EcoRI site separating them. This SalI-BamHI fragment with the PvuII and EcoRI sites was cloned into SalI and BamHI cleaved pAT153.7 (pAT153 with its EcoRI site deleted by filling in; also called pAT3404) yielding pAT3408.

Figure 4:
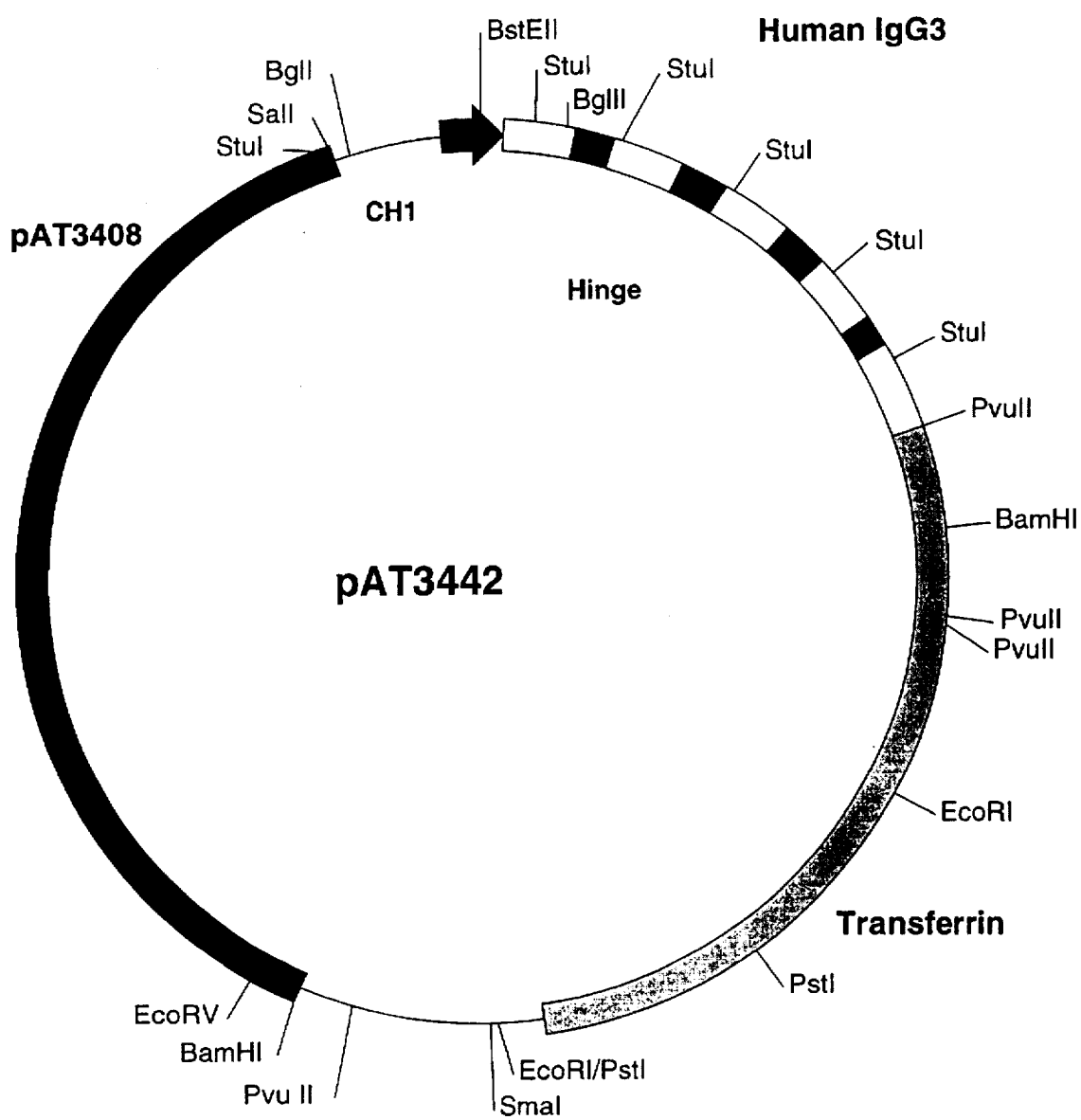
FIG. 4 is a restriction enzyme map of bacterial plasmid pAT3442 which additionally shows the human IgG3 and transferrin gene regions.

A 2.4 kb Pst I fragment containing the human transferrin cDNA sequence was isolated from clone Tf (U.S. Pat. No. 5,026,651) and cloned into the PstI site of pBluescript II KS [Stratagene] creating pKS3436. A PvuII site was introduced at the 3' end of the leader sequence of the transferrin by standard site-directed mutagenesis procedures, thereby creating pKS3438. An EcoRI site beyond the 3' end of the transferrin gene and the newly introduced PvuII site were used to clone the 2.4 kb fragment containing the transferrin coding sequence with its associated polyA site into pAT3408; transferrin thereby replaced the CH2 and CH3 domains of IgG3. As a consequence of this manipulation, a nucleotide sequence encoding the amino acid sequence ala-ala precedes the mature transferrin coding sequence. Approximately 600 bp of the region 3' of IgG3 adjacent to the BamHI site were adjacent to the 3' end of the transferrin gene. The resulting plasmid was designated pAT3442 (FIG. 4).

Figure 5A:
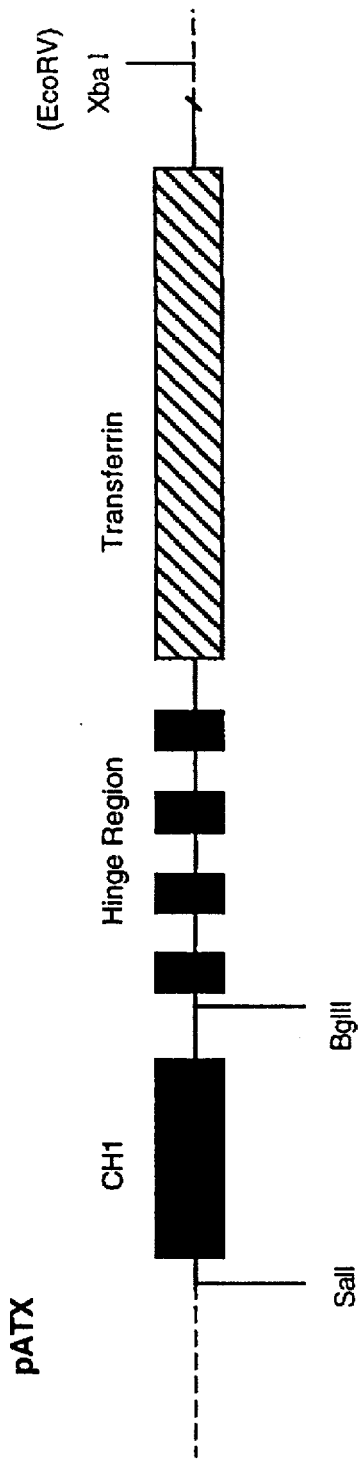
FIG. 5A is a restriction enzyme map of the CH1-hinge-transferrin region of clone pATX.

The unique Eco RV site downstream of the 3' untranslated IgG3 sequences in plasmid pAT3442 was converted to an XbaI site by digestion with EcoRV and ligation of a synthetic linker containing an XbaI restriction site in order to facilitate future cloning into appropriate mammalian vectors. A clone containing the new XbaI site was designated pATX. A map of the CH1-hinge-transferrin (CH1-hinge-Tf) region of pATX is shown in FIG. 5A.

The CH1 coding sequence in pATX was then replaced with the NGF gene. pATX was modified using polymerase chain reaction (PCR) techniques in two steps. The 5' PCR primer, HTF-1 (shown below), contained SalI and XhoI cloning sites near its 5' end, and 14 bases complementary to the first intron of the hinge region at its 3' end.

```
              SalI     XhoI    first hinge intron
HTF-1 5'-GG GTCGAG CTCGAC GGT GAG AGG CCA GC-3'
      (SEQ. ID. NO. 1)
```

The 3' primer (HTF-2) was complementary to a sequence within the first intron of the hinge region, approximately 400 nucleotides downstream of the 5' primer, and included a BglII cloning site.

```
         first hinge intron    BglII
HTF-2 5'-GGAGTTACTC AGATCT GGGAAG-3'
      (SEQ. ID. NO. 2)
```

Figure 5B:
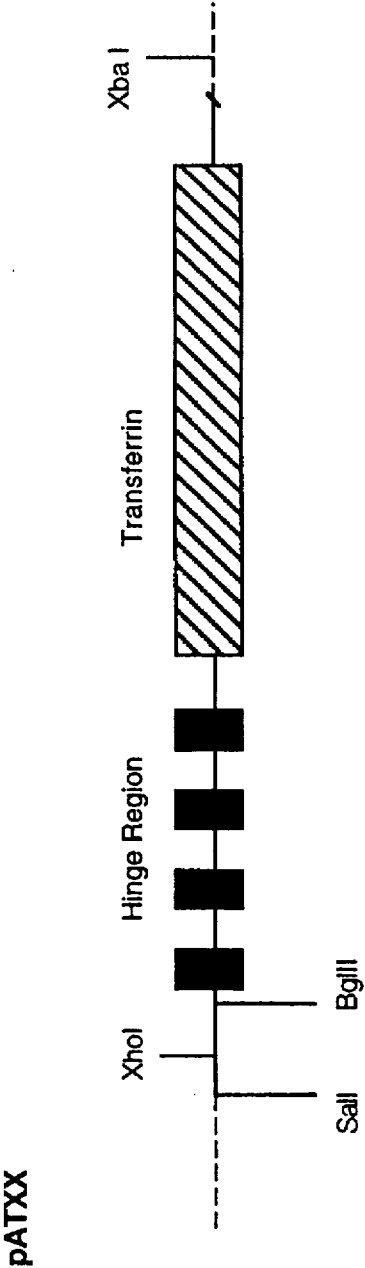
FIG. 5B is a restriction enzyme map of the CH1-hinge-transferrin region of clone pATXX.

The primers were combined with pATX template DNA and, following the PCR procedures, the 400 bp amplified fragment was gel purified, digested with SalI and BglII, and cloned into pATX which had been digested to completion with SalI and partially with BglII (to cleave at one of two BglII sites of this plasmid). The ligated sample was transformed into E. coli DH1 cells and a clone having the 400 bp ligated fragment in place of the CH1 region was identified by restriction digestion analysis. This clone was designated pATXX; a map of the hinge-transferrin region of pATXX is shown in FIG. 5B.

Isolation and Cloning of the NGF Gene

The pre-pro form of the NGF gene, which is about twice the size of the mature β-NGF coding sequence and contains the signals for protein secretion and protein folding, was amplified by PCR techniques from human erythrocyte genomic DNA (purchased from Clontech, Palo Alto, Calif.) using the following primers.

```
PNGF 1 (5' Primer)
       HindIII    XhoI    XbaI                       Start
5'-G AAGCTT CTCGAG TCTAGA CCAGGTGCATAGCGTA ATG TCC-3'
    (SEQ. ID. NO. 3)

PNGF 2 (3' Primer)
     SalI    XhoI
5'-C GTCGAC CTCGAG TCTCACAGCCTTCCTGCTGAGC-3'
    (SEQ. ID. NO. 4)
```

PNGF1 and PNGF2 were partially homologous to sequences at the 5' and 3' ends of the pre-pro NGF gene, respectively, and were devised to create XhoI cloning sites at either end of the NGF gene. The 5' primer additionally contained an XbaI cloning site.

Figure 5C:
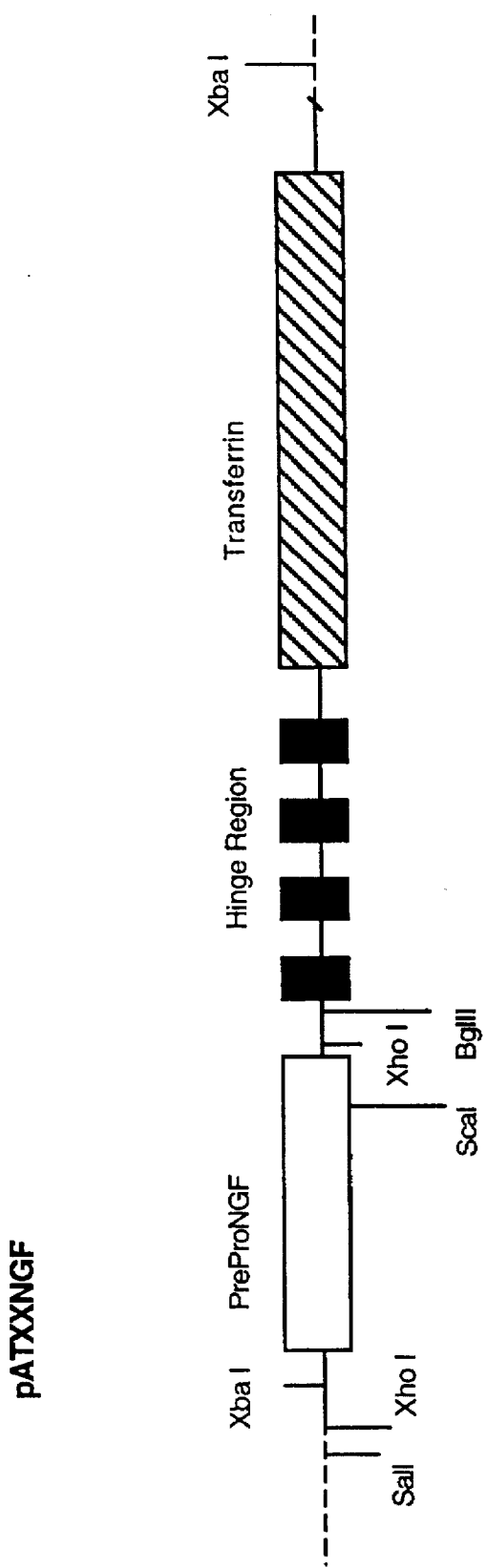
FIG. 5C is a restriction enzyme map of the pre-pro NGF-hinge-transferrin region of clone pATXXNGF.

Using the PNGF1 and PNGF2 primers, a fragment of approximately 800 bp containing the pre-pro NGF gene was amplified. The resulting DNA was digested with XhoI, and the (approximately) 800 bp fragment was gel purified and ligated into XhoI digested pATXX. A clone designated pATXXNGF was identified which had the pre-pro NGF gene inserted upstream and adjacent to the IgG3 hinge region in the same orientation as the transferrin gene thereby creating an NGF-IgG3 hinge-transferrin (NHT) gene fusion. A map of this region of pATXXNGF is shown in FIG. 5C. (The XhoI site 3' to the pre-pro NGF coding region of pATXXNGF encodes a leu-glu which precedes the IgG3 hinge region).

A partial DNA sequence of the junctions between the NGF-hinge and hinge-transferrin sequences were determined in order to verify the sequence of the primers and to confirm the correct reading frame within the newly formed gene fusion. The determined sequences revealed one nucleotide change, a G to A transition, which resulted in an arginine to glutamine change at amino acid position 80 in the pre-pro portion of NGF.

Reconstruction of the NGF-Hinge-Transferrin Genetic Fusion in Mammalian Expression Vectors The NGF-IgG3 hinge-transferrin gene fusion was cloned stepwise into mammalian expression vector pcDNAI/AMP (Invitrogen) for transfection into COS cells (ATCC Accession Number CRL 1651) using the following procedure.

The pre-pro NGF portion of the gene fusion was first amplified from pATXXNGF using PCR techniques. The 5' PCR primer, PNGF1, was described above and the 3' PCR primer, PNGF3, is shown below.

```
PNGF3 (3' Primer)
    SalI       XbaI
5'-C GTCGAC TCTAGA TTA TCTCACAGCCTTC-3'
                   Stop
(SEQ. ID. NO. 5)
```

Figure 6:
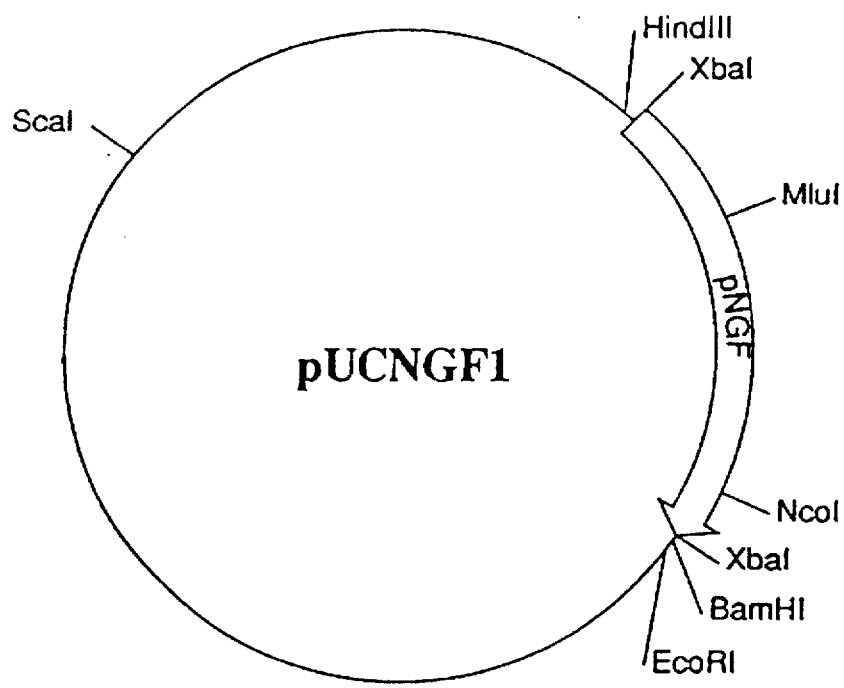
FIG. 6 is a restriction enzyme map of clones pUCNGF1 and pUCNGF2 which contain the NGF gene in opposite orientations.
Figure 6:
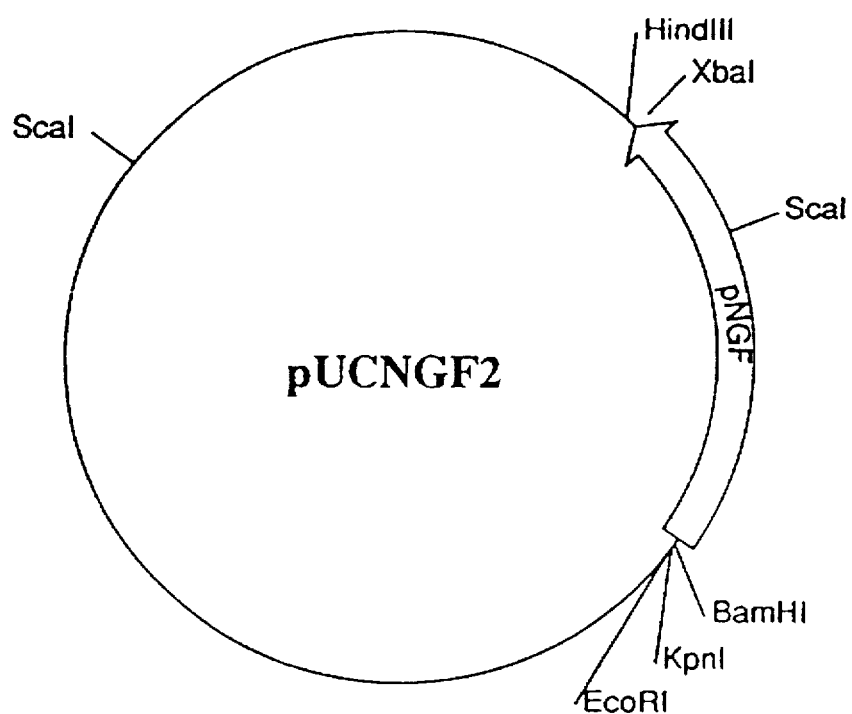

Using the PNGF1 and PNGF3 primers, an approximately 800 bp fragment containing the pre-pro NGF gene was amplified from pATXXNGF. The resulting DNA was digested with XbaI, ligated into XbaI digested bacterial vector pUC18 (Boehringer-Mannheim) and transformed into competent *E. coli* TOP10F cells (Invitrogen). Clones containing the NGF gene in either orientation were identified by restriction analysis and designated pUCNGF1 (clockwise orientation) and pUCNGF2 (counterclockwise orientation) (FIG. 6).

Figure 7:
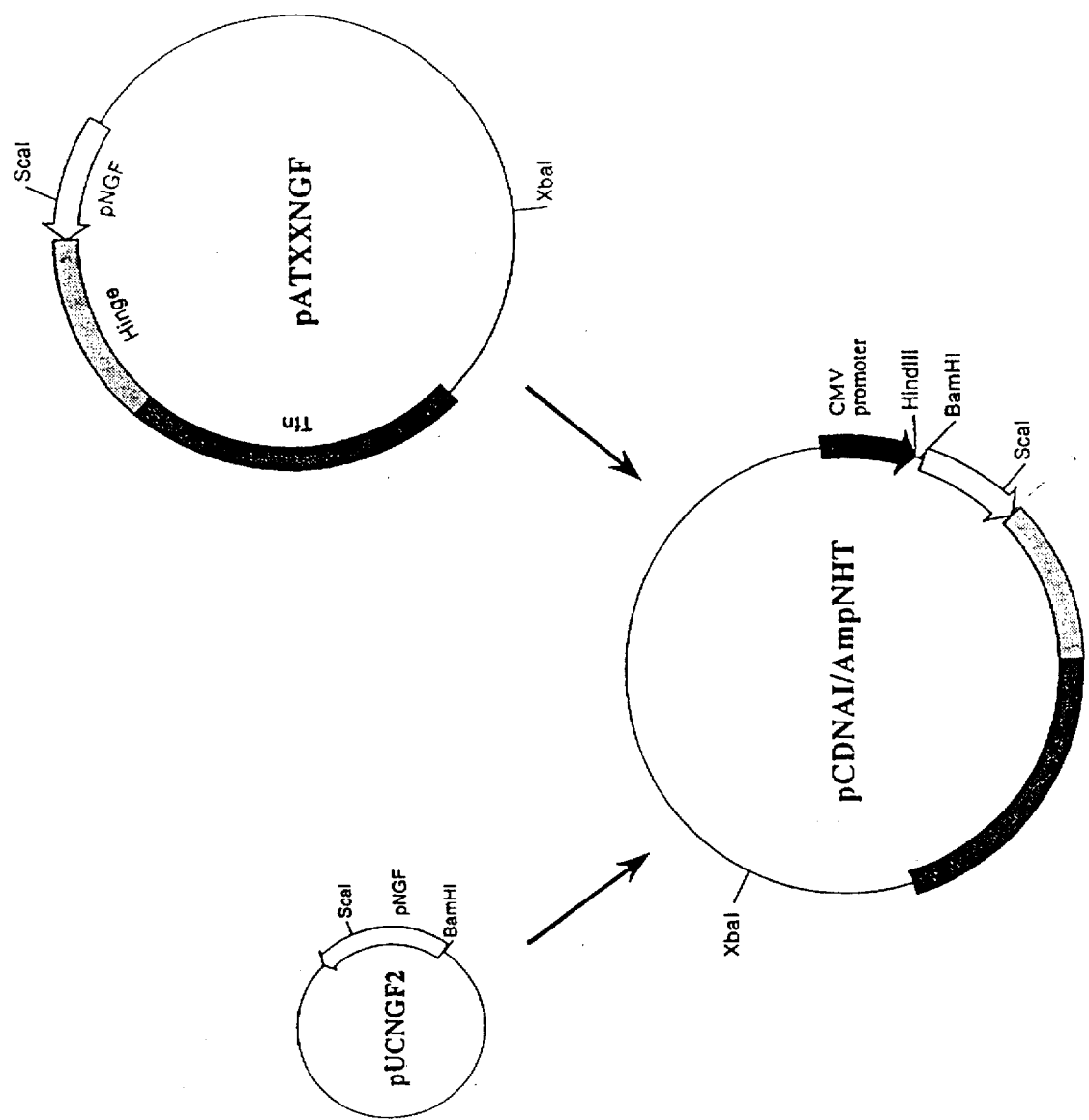
FIG. 7 is a set of restriction enzyme maps that depict the formation of plasmid pcDNAI/AmpNHT with fragments from clones pUCNGF2 and pATXXNGF.

The entire NHT gene fusion was then recreated in pcDNAI/Amp using a three-part ligation. The first fragment, an approximately 600 bp fragment containing most of the NGF gene, was removed from pUCNGF2 by digestion with BamHI, which cleaves within the polylinker sequence upstream of the pre-pro NGF gene sequence, and ScaI, which cleaves near the 3' end of the NGF gene. The second fragment was a 4.7 kb ScaI to XbaI fragment isolated from pATXXNGF which contained the remainder of the 3' end of the NGF gene, the hinge region and the entire transferrin gene. The third fragment was the pcDNAI/Amp vector which had been digested within its polylinker sequence with BamHI and XbaI and gel purified. The three fragments were ligated together (FIG. 7) and transformed into *E. coli* cells. A plasmid containing all three fragments was identified and designated pcDNAI/AmpNHT. The DNA sequence was again determined to verify the NGF and transferrin coding sequences. The determined sequence revealed a T to C transition in NGF which resulted in a valine to alanine change at amino acid 35, and three changes from the published transferrin nucleotide sequence that did not result in amino acid changes.

Assay for NGF and Transferrin in the Fusion Protein Expressed in Mammalian Cells Expression plasmid pcDNAI/AmpNHT was transfected and transiently expressed in COS cells. The fusion protein in culture supernatants was detected using anti-NGF antibodies, anti-transferrin antibodies, or purified transferrin receptor by standard ELISA procedures.

Briefly, capture antibody (anti-NGF or anti-transferrin), which was specific for either the NGF or transferrin portions of the fusion protein, was coated in the wells of a 96-well plate. The wells were washed (PBS-0.05% Tween), blocked with 1% bovine serum albumin (BSA), and supernatants from transfected COS cells were added to the wells (typically in serial four-fold dilutions) and incubated for one hour at room temperature.

A detection antibody was chosen which would recognize the other portion of the fusion protein (either anti-Tf or anti-NGF) and was added to the wells on top of the fusion protein. Bound antibody was detected after amplification of the signals by an avidin-biotin reaction using the Vectastain ABC kit (VectorLabs). Protein was quantitated by extrapolation from standard curves generated for known concentrations of NGF or transferrin.

Alternative ELISA procedures may be used to detect and quantitate the fusion proteins. For example, the capture antibody and detection antibody may recognize the same portion of the fusion protein.

Optimization of Expression of the NHT Fusion Proteins

In order to increase the level of expression of the NHT fusion protein, the translation initiation sequence immediately preceding the AUG start codon of the pre-pro NGF gene was modified using PCR techniques to incorporate a Kozak consensus sequence (Kozak, 1987, *Nucl. Acid. Res.* 15, 8125).

Two PCR primers were designed which were complementary to regions flanking the pre-pro NGF gene sequence. The 5' primer, p45.1, contained an SmaI restriction site as well as the sequence CCACC, the Kozak sequence, which has been shown to be important for efficient translation in mammalian cells, immediately preceding the ATG initiation codon of the pre-pro NGF gene.

```
p45.1
      SmaI        XbaI         Kozak
5'-TCC CCCGGG TCTAGA CCAGGTGCAT CCACC ATGTCCATGTTGTTC-3'
                    (SEQ. ID. NO. 6)
```

The 3' primer, p16.1, was complementary to a sequence 3' to both the NGF coding sequence and the BamHI site in pUCNGF1.

```
P16.1
5'-AACAGCTATGACCATG-3'
(SEQ. ID. NO. 7)
```

By PCR techniques, the pre-pro NGF coding sequence, preceded by the Kozak translation initiation consensus sequence in p45.1, was amplified from pUCNGF1 using the p45.1 and p16.1 primers. The resulting DNA can be cloned into the mammalian expression vector, CD51neg1.

One way to accomplish this cloning is to first insert the pre-pro NGF gene sequence into a bacterial vector, for example pGEM-2 (Promega), having compatible restriction sites for subsequent cloning into the mammalian expression vector. The amplified pre-pro NGF gene can be digested with SmaI and BamHI and ligated into the polylinker of pGEM-2 between HincII and BamHI sites (since SmaI and HincII produce blunt-ended fragments) thereby producing a clone designated pGEM-2/KNGF.

The NHT fusion is then recreated by a three-part ligation as follows. A HindIII-ScaI fragment from the pGEM-2/KNGF clone (containing most of the NGF coding region) is mixed with the ScaI-XbaI fragment from pcDNAI/AmpNHT (containing the C-terminal-most portion of the NGF gene, the IgG3 hinge and the transferrin coding sequence) and HindIII+XbaI digested pGEM-2 vector. The resulting vector has the entire NHT fusion between flanking XbaI sites (the 5' XbaI site from linker p45.1). This XbaI fragment is then cloned into the XbaI digested CD5lneg1.

Figure 8:
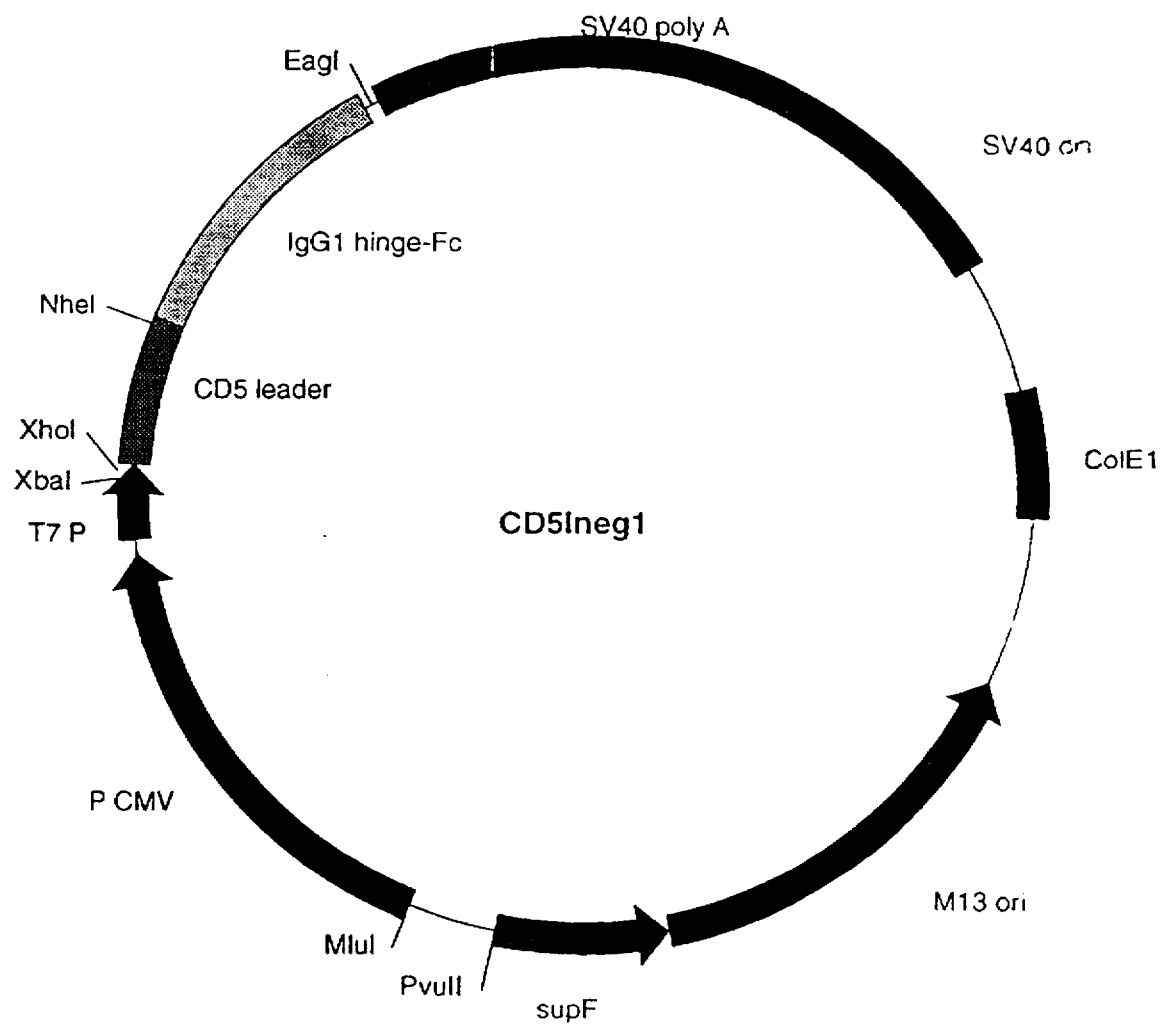
FIG. 8 is a restriction enzyme map of clone CD51neg1.

CD5lneg1 contains a CMV promoter sequence, a CD5 leader sequence for secretion of a cloned protein, a sequence encoding the hinge region and Fc portion of IgG1, and a polyadenylation signal sequence (FIG. 8).

CD5lneg1 (gift of Brian Seed, Massachusetts General Hospital) can be derived from plasmid pCDM8 (Invitrogen) by deletion of the 590 bp DraI fragment within the SV40 intron sequence, the BamHI-SfiI fragment containing the polyoma origin of replication, and a 20 bp NheI-SspI fragment at the 3' end of M13 ori which was removed in order to eliminate the NheI site. In addition, CD5lneg1 also contains the CD5 leader sequence (Genbank reference number X04391) adjacent to the IgG1 hinge-Fc region (Genbank reference number J00228) inserted between the XhoI (within polylinker) and EagI (approximately 43 bp beyond polylinker) sites of pCDM8. The DNA sequence of the IgG1 hinge region between the XhoI and EagI sites is shown in FIGS. 9A and 9B (Seq. I.D.NO.8). The CD5 leader sequence and IgG1 exons are indicated on this figure. The clone resulting from the insertion of the entire NHT fusion into CD5lneg1 is designated CD5KNHT.

Vector CD5KNHT was transfected into CHO cells and expression of the fusion protein was assayed by ELISA as described above. Proteins containing both the transferrin and NGF sequences were expressed and detected in the culture supernatant.

Purification of NGF-Hinge-Transferrin Fusion Protein from COS Cell Supernatants.

NGF-hinge-transferrin fusion protein present in the supernatant of transfected COS cells was purified using an anti-NGF affinity column. Medium from cells transfected with CD5KNHT was loaded overnight by gravity onto a Sepharose column to which rat anti-mouse NGF monoclonal antibody had been bound (e.g., antibody 1G3, Saffron et al., *Brain Res.* 1989, 492:245–254). This column had been pre-equilibrated with PBS. The columns were washed five times with 2 ml PBS, and NGF containing proteins were eluted with 10 ml of a 0.1M glycine, 0.15M NaCl solution, pH 3.0. The elution was accomplished as five 2 ml fractions which were placed directly into tubes containing 50 µl 1M $NH_4HCO_3$ and 8 µg/ml $FeNH_4$ citrate. The $OD_{280}$ of each of the fractions was then determined.

The affinity purified fractions contained a major band at MW 100 kD on a reducing SDS-polyacrylamide gel. The band was recognized by anti-transferrin antibody and anti-NGF antibody.

In vitro Competition Assay for Transferrin Receptor Binding Activity

A critical attribute of the NHT fusion protein is its ability to bind to the transferrin receptor. Assays were performed to measure the affinity of the NHT fusion protein for the human transferrin receptor by the ability of the fusion protein to compete with native transferrin for binding to the transferrin receptor.

Transferrin receptor was purified from freshly obtained full term human placentas using the procedure of Turkewitz et al. (1988, *J. Biol. Chem.*, 263: 8318–8325). Briefly, placental membranes were isolated and stored frozen at −80° C. Frozen membranes were thawed and extracted with detergent. Endogenous iron was chelated, greatly lowering the affinity of endogenous transferrin for the receptor. The transferrin receptor was then purified on a human transferrin-Sepharose column. By gel analysis, the resulting receptor had the expected molecular weight, and the purity, as determined by scanning densitometry of the gel, was 98%. The purified transferrin receptor was immunoblotted using antibody 128.1 and another commercially obtained anti-human transferrin receptor antibody (Amersham RPN. 511).

Figure 10:
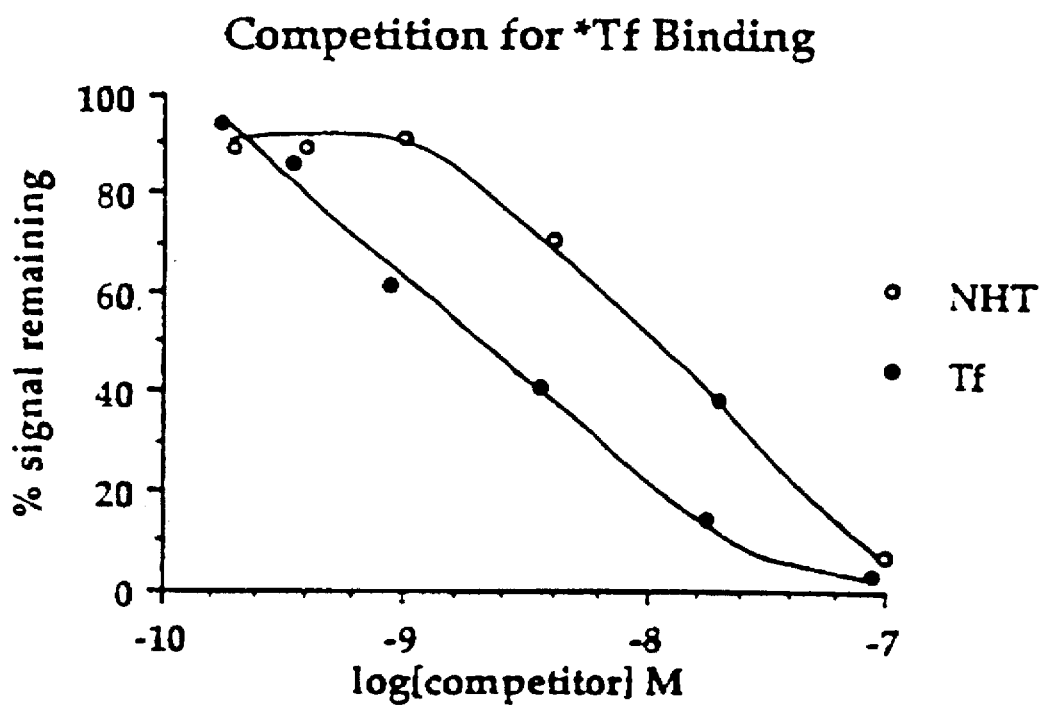
FIG. 10 is a graphic representation of the competition between either recombinant human transferrin or NHT fusion protein and radioactively labeled transferrin when binding to human placental transferrin receptors.

For the competition assay, microtiter wells were coated with 100 µl/well of 0.7 µg/ml purified human placental transferrin receptor in coating buffer (10 mM sodium carbonate, pH 9.5) overnight at 4° C. Nonspecific binding was blocked by incubation with 200 µl/well of 1% w/v bovine serum albumin (BSA) for 1 hour at 37° C. The wells were then washed, and 100 µl of a mixture of 4 nM $^{125}$I-transferrin (New England Nuclear) and varying concentrations of competitor, either purified recombinant human transferrin or NHT fusion protein, were applied to each well and incubated for 1 hour at room temperature. After washing, the wells were individually counted using a gamma counter. The percent signal remaining versus competitor concentration was plotted and the point of 50% remaining signal was determined (FIG. 10). The results demonstrated that the NGF-hinge-transferrin fusion protein binds to the human transferrin receptor but has reduced affinity for this receptor compared to native human transferrin.

In vitro Assay for NGF Activity

A clonal line of rat pheochromocytoma cells (designated PC12) undergoes cessation of cell division and extensive outgrowth of neurite-like processes in the presence of NGF in vitro. This cell-based bioassay was used to assess whether the expressed NHT fusion protein has NGF activity by measuring its ability to stimulate neurite outgrowth.

PC12 cells were grown in RPMI 1640 medium (Bio Whittaker) containing 5% fetal calf serum, 10% horse serum and 2 mM L-glutamine, in T75 flasks under 5% $CO_2$. Ninety-six well plates were coated with 0.5 µg/cm$^2$ bovine collagen IV at 50 µl/well, air dried overnight and exposed to UV light for 20 minutes prior to use. Five ml of PC12 cells were removed from each flask and forced through a 21 g needle about 5–10 times to break up clumps. This procedure caused the cells to lose their neurites. The cells were diluted with media to approximately $2 \times 10^4$ cells/ml, 50 µl were added to each well of the collagen-coated plates (1000 cells/well), and incubated for 1–2 hours to allow the cells to attach.

Figure 11A:
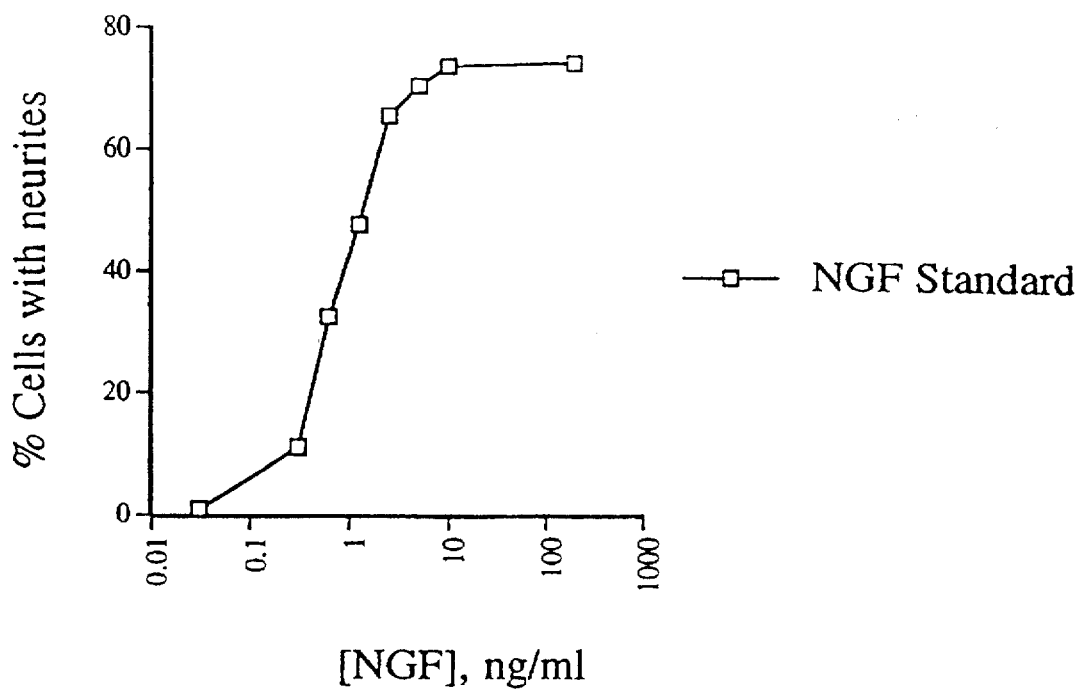
FIG. 11A is a graphic representation of the inducing effect of NGF on the sprouting of neurites from PC12 cells.
Figure 11B:
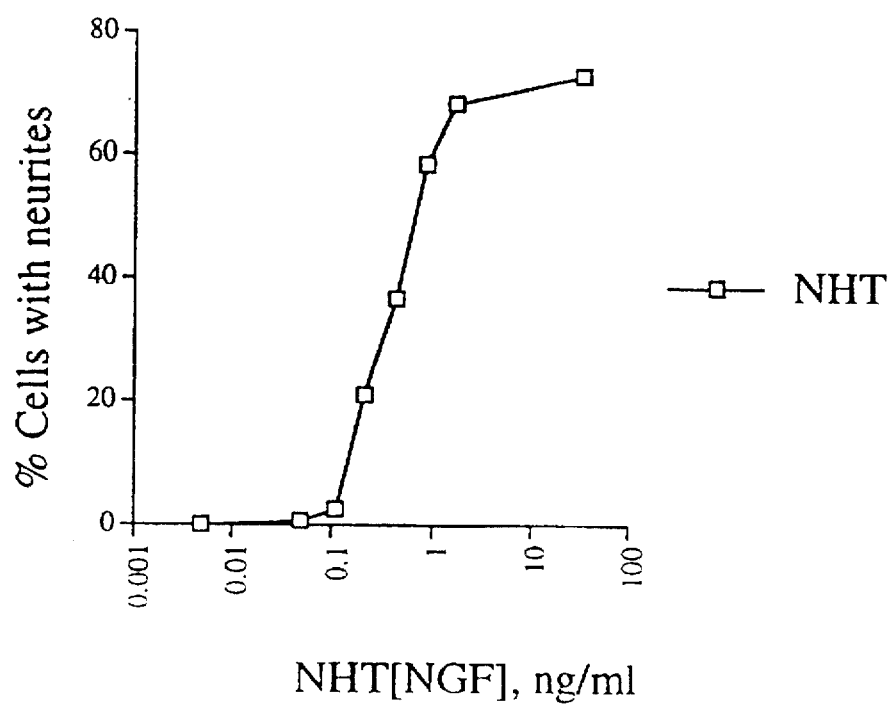
FIG. 11B is a graphic representation of the inducing effect of NHT fusion protein on the sprouting of neurites from PC12 cells.

Samples to be tested were filter sterilized before use. To generate a dose-response curve, the samples were serially diluted in two-fold increments in growth medium and 50 µl samples were added to the wells. Purified mouse NGF was serially diluted and plated in the same manner to generate a standard curve. After 5 days exposure to the NGF-containing samples, plates were scored for the presence or absence of NGF activity by counting the total number of cells and the number of cells sprouting at least one neurite that is longer than twice the diameter of the cell body in two or three representative fields of view. The results were expressed as the percent of cells extending neurites as a function of NGF concentration (FIG. 11). Panel A is the standard curve for purified mouse NGF. Panel B is the activity curve for the NHT fusion protein. The results demonstrated that the fusion protein fully retained NGF biological activity in vitro.

EXAMPLE 12

Construction of Other NGF-Transferrin Fusion Genes

Three additional fusions of NGF and transferrin were created and tested: 1) a direct fusion of the pre-pro NGF gene and transferrin cDNA, 2)a fusion of the pre-pro NGF gene and transferrin cDNA separated by a sequence encoding five glycine residues (NGF-(gly)$_5$-transferrin), and 3) a fusion of the pre-pro NGF gene and transferrin cDNA separated by a sequence encoding leu-glu (NGF-leu-glu-transferrin). The NGF-IgG3 hinge-transferrin containing vector, CD5KNHT, was employed as the source of genetic material for creating these fusions.

Two-step PCR reactions were performed on CD5KNHT to generate the NGF-transferrin direct fusion and the NGF-(gly)$_5$-transferrin fusion. For NGF-leu glu-transferrin, a one-step PCR reaction was sufficient to generate the fragment of interest. Methods for constructing each of these gene fusions are described below.

Construction of the NGF-Tf Direct Fusion

The following PCR primers were used:

P202 5'-AAGGAGGTGATGGTGTTGGGA-3'
(SEQ. ID. NO. 9)

5'end of transferrin/3' end of NGF
P205 5'-CTCACAGTTTTATCAGGGAC TCTCACAGCCTTCCTG CTGAGC-3'
SEQ. ID. NO. 10)

3' end of NGF/5' end of transferrin
P204 5'-CAGCAGGAAGGCTGTGAGA GTCCCTGATAAAACTGT GAGATG-3'
(SEQ. ID. NO. 11)

P203 5'-GTGTGGCAGGACTTCTTGCCT-3'
(SEQ. ID. NO. 12)

P202 and P205 were primers used to amplify the 3' two-thirds of the NGF gene. P202 was complementary to a sequence within the NGF gene 5' to the unique ScaI site. P205 was complementary to 22 bases at the 3' end of the NGF gene, and 20 bases at the 5' end of the transferrin gene.

Primers P204 and P203 were used to amplify the transferrin gene. P204 was complementary to a 23 base sequence at the 5' end of the transferrin gene and 19 bases at the 3' end of the NGF gene. P203 was complementary to a sequence within the transferrin coding sequence 3' to a unique BamHI site.

pcDNAI/AmpNHT DNA was mixed separately with the two sets of primers. As a result of PCR, two fragments were amplified having overlapping protrusions creating the junction between the NGF and transferrin coding sequences. The two fragments were gel purified and an equimolar amount of each fragment was combined for a second PCR amplification with primers P202 and P203. The resulting product was digested with ScaI and BamHI and exchanged with the comparable ScaI to BamHI fragment of CD5KNHT DNA that included the 3' end of the NGF gene, the hinge region and the 5' end of transferrin coding sequence. (The BamHI digestion of CD5KNHT was a partial digestion due to the presence of a second BamHI site downstream of the transferrin gene.) The resulting plasmid, CD5KNT, contained a direct fusion of the NGF and transferrin genes.

Construction of the NGF-(Gly)$_5$-Transferrin Fusion

The following PCR primers were used: P202 (SEQ.ID. NO. 9), P200, P201 and P203 (SEQ.ID.NO.12).

P200  3' end of NGF/  Gly$_5$  /
5'-CAGCAGGAAGGCTGTGAGA GGGGGAGGTGGAGGG
5' end of tranferrin
GTCCCTGATAAAACTGTGAGATG-3'
(SEQ. ID. NO. 13)

P201  5' end of transferrin/  Gly$_5$  /
5'-CTCACAGTTTTATCAGGGAC CCCTCCACCTCCCCC T
3' end of NGF
CTCACAGCCTTC-3'
(SEQ. ID. NO. 14)

Primer P200 was in part complementary to the 3' end of the NGF gene and contained a non-complementary region encoding five glycine residues followed by 23 bases complementary to the 5' end of the transferrin coding sequence. Primer P201 was complementary to the 5' end of the transferrin, preceded by a non-complementary region encoding five glycine residues and the 3' end of the NGF gene.

pcDNAI/AmpNHT DNA was mixed separately with the two sets of primers (P202 and P201 were used to amplify the 3' two-thirds of the NGF gene and P200 and P203 were used to amplify the 5' end of the transferrin gene). Two fragments were generated having overlapping protrusions. The two fragments were gel purified and an equimolar amount of each fragment was combined for a second PCR amplification with primers P202 and P203. The resulting amplified product was digested with ScaI and BamHI and exchanged for the comparable ScaI to BamHI fragment of CD5KNHT DNA as described above. The resulting plasmid, CD5KNGT, contained a fusion of the NGF and transferrin coding sequences separated by a sequence encoding five glycine residues.

Construction of the NGF-leu glu-Transferrin Fusion

The following primers were used: P206 and P203 (SEQ. ID.NO.12).

P206  XhoI  /5' end of transferrin
5'-GGAACGGC CTCGAG GTCCCTGATAAAACTGTGAGA-3'
(SEQ. ID. NO. 15)

Primer P206 contained an XhoI site (CTCGAG which encodes Leu-Glu) followed immediately by a 21 base sequence complementary to the 5' end of transferrin coding sequence. Primer P203 is complementary to the region 3' to the BamHI site within the transferrin gene. pcDNAI/AmpNHT DNA was combined with the two primers for PCR amplification. The resulting fragment was digested with XhoI and BamHI and ligated with CD5KNHT that had been digested to completion with XhoI and partially with BamHI, resulting in the deletion of the IgG3 hinge region and inclusion of a leu-glu coding sequence. The resulting plasmid, CD5KNXT, contained a fusion of the NGF and transferrin coding sequence separated by a sequence encoding leu-glu.

The NGF-transferrin direct fusion, NGF-(Gly)$_5$-transferrin fusion, and NGF-leu glu-transferrin fusion were each transfected and transiently expressed in COS cells as in Example 11. Each of the expressed fusion proteins were detected by using anti-NGF antibodies, anti-transferrin antibodies or purified transferrin receptors. This demonstrates that these fusion proteins have NGF and transferrin binding characteristics similar to that of the native unfused proteins.

These three fusion proteins were also subjected to the PC12 neurite outgrowth bioassay for NGF activity as described in Example 11. Each of the three fusion proteins exhibited NGF biological activity as exemplified by their ability to stimulate neurite outgrowth.

EXAMPLE 13

Construction of a CNTF-Transferrin Fusion Gene

Isolation and Cloning of CNTF Gene

The human CNTF gene was cloned from genomic DNA prepared from Jurket cells using PCR techniques. To obtain the CNTF gene sequence uninterrupted by intron sequences, PCR was performed in two steps using the following four primers.

P31.1     NdeI
5'-AGTTAA CATATG GCTTTTACTGAGCATTCAC-3'
(SEQ. ID. NO. 16)

P42.1
5'-CAGGCCCTGATGCTTCACATAGGATTCCGTAAGAGC
AGT-3'
(SEQ. ID. NO. 17)

p35.1
5'-TACGGAATCCTATGTGAAGCATCAGGGCCTGA ACA-3'
(SEQ. ID. NO. 18)

P42.2     XhoI
5'-GGGCC CTCGAG GGACTAACTGCTACATTTTCTTGTT
GTT AGC-3'
(SEQ. ID. NO. 19)

P31.1 and P42.1 were the 5' and 3' primers for amplifying the 5' exon of CNTF. P31.1 was complementary to the 5' end of the 5' exon and contained an NdeI cloning site. P42.1 contained 21 bases complementary to the 3' end of the 5' exon and 18 bases complementary to the 5' end of the 3' exon.

P35.1 and P42.2 were the 5' and 3' primers for amplification of the 3' exon of CNTF. P35.1 was complementary to the 3' exon and contained 13 additional bases which were complementary to the 3' end of the 5' exon. P42.2 was complementary to the 3' end of the 3' exon and contained an XhoI cloning site.

Genomic DNA was mixed separately with the two sets of primers. A 120 bp fragment was amplified with primers P31.1 and P42.1, and a 480 bp fragment was amplified with primers P35.1 and P42.2. The two fragments had a total of 31 base pairs of overlapping sequence.

In the second PCR reaction, a 600 bp fragment was amplified using a mixture of gel purified 120 bp and 480 bp fragments as templates together with primers P31.1 and P42.2 (described above). The amplified fragment was digested with NdeI and XhoI and gel purified.

The NdeI-XhoI fragment was cloned into E. coli expression vector pET17xB (Novagen) that had been gel isolated after digestion with NdeI and XhoI. The ligated product was transformed into competent E. coli MC1061 cells. A clone containing the CNTF gene fragment was identified by restriction digestion and DNA sequence analysis and designated J6.

Cloning of Human CNTF Coding Sequence into a Mammalian Expression Vector

The human CNTF coding sequence was cloned into the CD51neg1 mammalian expression vector of Example 12. By the methods described below, the CNTF gene was cloned into the CD51neg1 expression vector, adjacent to the CD5 leader sequence, in place of the IgG1 sequences.

To prepare CNTF DNA having terminal restriction sites compatible with sites in CD51neg1, a DNA fragment was generated by PCR techniques using clone J6 as a template and P33.1 and P35.2 as 5' and 3' PCR primers, respectively. P33.1 was complementary to the 5' end of the CNTF gene and contained a BlnI restriction site rather than the NdeI site. P35.2 was, in part, complementary to the 3' end of the CNTF gene and contained an EagI restriction site rather than the XhoI site.

P33.1     BlnI
5'-CGCGGG CCTAGG CGCTTTCACAGAGCATTCACC-3'
(SEQ. ID. NO. 20)

P35.2     EagI
5'CGCGGGG CGGCCG CTTTACATTTTCTTGTTGTTGTTAG-3'
(SEQ. ID. NO. 21)

Following PCR, the resulting amplified DNA fragment was treated with BlnI and EagI and ligated with the NheI and EagI digested CD51neg1 vector backbone (NheI and BlnI generate compatable protrusions; neither site is regenerated after ligation). The ligated mixture was transformed into competent E. coli MC1061 cells. A resulting clone having the CNTF gene preceeded by the CMV promoter and CD5 leader was identified by restriction digestion and designated D1.

Figure 12A:
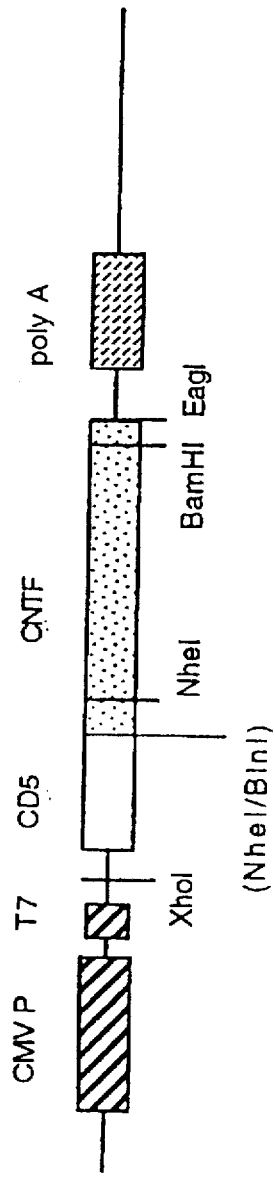
FIG. 12A is a restriction enzyme map of plasmids D1 and d1.

In order to minimize the possibility that the CNTF gene present in plasmid D1 contained mutations resulting from PCR procedures, NheI and BamHI, each of which cleaves once within CNTF, were used to isolate a fragment containing most of the CNTF coding sequence from D1 and exchanged for the equivalent NheI-BamHI fragment of CNTF from J6. The resulting plasmid was designated d1 (see FIG. 12A).

Construction of CNTF-Transferrin Gene Fusions

Three different gene fusions encoding CNTF-transferrin fusion proteins were constructed. In each case, the proteins were connected by different linking sequences. In the first of these constructs, CNTF and transferrin were connected by the hinge region of IgG3 (CNTF-IgG3 hinge-transferrin). In the second construct, the CNTF and the transferrin sequences were joined without an intervening linker (CNTF-transferrin). In the third construct, a sequence coding for penta-glycine was inserted between the CNTF and transferrin genes (CNTF-(Gly)$_5$-transferrin). Methods for constructing each of these gene fusions are described below.

A. CNTF-IgG3 Hinge-Transferrin

The gene fusion coding for CNTF-IgG3 hinge-transferrin was constructed for expression in the CD51neg1 expression vector using the following multi-step procedure. First, the transferrin gene was isolated and cloned into CD51neg1 in place of the IgG1 sequences. To do this, a fragment containing the transferrin gene was generated by PCR techniques using pcDNAI/AmpNHT of Example 11 as the template and oligonucleotides P33.2 and P36.1 as 5' and 3' PCR primers, respectively. P33.2 was complementary to the 5' end of the transferrin gene and contained a BlnI site. P36.1 was complementary to the 3' end of the gene and contained an EagI site.

```
P33.2         BlnI
  5'-GCTTCCGT CCTACG GGTCCCTGATAAAACTGTG-3'
  (SEQ. ID. NO. 22)

P36.1         EagI
  5-CGCGGGG CGGCCG CTTTAAGGTCTACGGAAAGTGCA-3'
  (SEQ. ID. NO. 23)
```

Figure 12B:
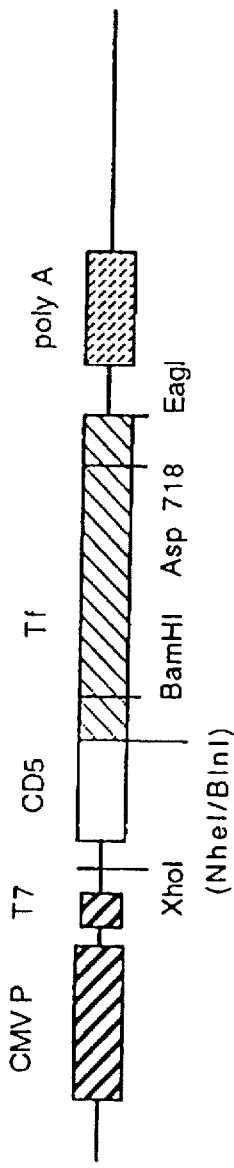
FIG. 12B is a restriction enzyme map of plasmids C4 and C*.

Following PCR, the amplified fragment was digested with BlnI and EagI and cloned into the NheI and EagI digested and gel purified CD51neg1 backbone. The resulting plasmid, having the transferrin gene inserted adjacent to and downstream of the CD5 leader in place of the IgG1 hinge-Fc, was designated C4. As before, in order to eliminate the possibility that errors may have been incorporated during PCR amplification, a BamHI to Asp718 fragment of C4, which contained most of the transferrin gene sequence, was replaced with the equivalent BamHI-Asp718 fragment of the starting plasmid pcDNAI/AmpNHT. The resulting plasmid was designated C*. (See FIG. 12B).

Figure 12C:
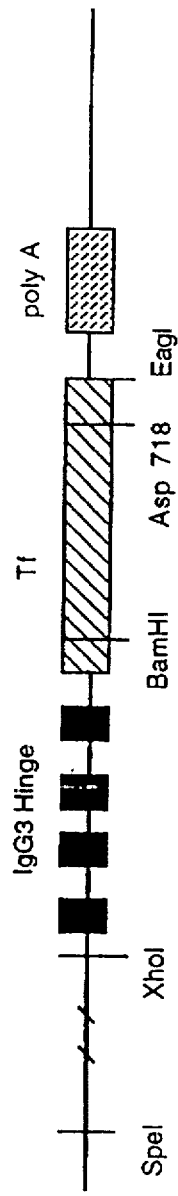
FIG. 12C is a restriction enzyme map of plasmid C4-NHT.

The IgG3 hinge region sequence was then inserted upstream of the transferrin coding sequence in C4 as follows. The XhoI-Asp718 fragment containing the IgG3 hinge and the 5' portion of the transferrin coding sequence (with the ala-ala coding sequence immediately upstream of the transferrin coding sequence) from pcDNAI/AmpNHT was isolated and cloned into the XhoI and Asp718 digested C4 backbone to generate C4-NHT. (See FIG. 12C).

Figure 12D:
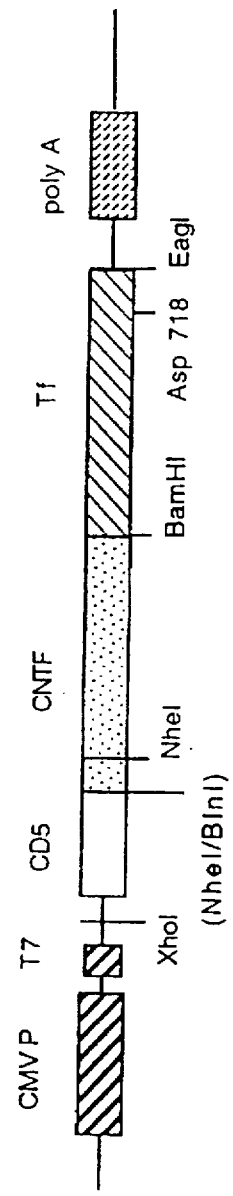
FIG. 12D is a restriction enzyme map of plasmid g*.

Next, a gene fusion consisting of the CNTF gene and the transferrin gene was created in the CD51neg1 backbone. First, a 0.7 kb XhoI-BamHI fragment from clone d1 (containing the CD5 leader and most of the CNTF gene except for the 3' end) and a 1.8 kb BamHI-EagI fragment from C4-NHT (containing most of the transferrin coding sequences except for the 5' end) were ligated with XhoI and EagI digested and gel-purified CD51neg1 backbone to generate g*. (See FIG. 12D).

Then, a fragment containing the IgG3 hinge region was inserted between the CNTF and transferrin genes. In order to accomplish this, an XhoI site was created at the 3' end of the CNTF gene to make it compatible with the XhoI site at the 5' end of the hinge region sequence. (This XhoI site encoded a leu-glu 5' to the IgG3 hinge region). A new CNTF containing fragment was generated by PCR techniques using J6 as the template and primers P33.1 (above) and P36.5 (containing an XhoI site).

```
              XhoI
P36.5  5'TGGCCTCTCACC CTCGAG CATTTTCTTGTTGTT
       AGC-3'
       (SEQ. ID. NO. 24)
```

Figure 12E:
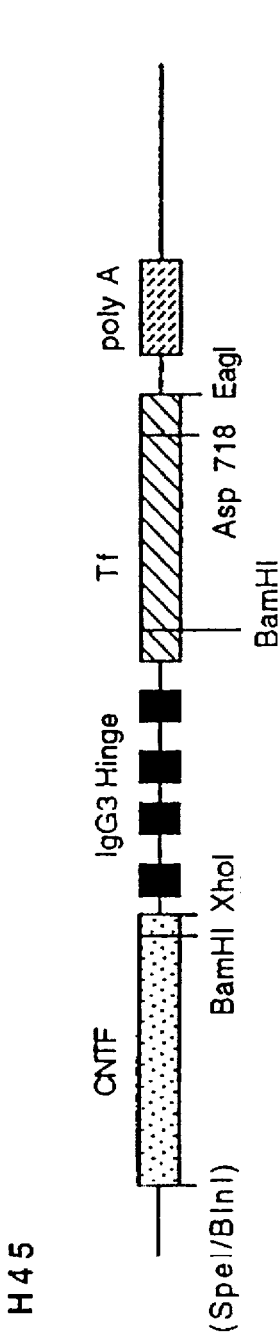
FIG. 12E is a restriction enzyme map of plasmid H45.

The PCR product was digested with BlnI and XhoI and cloned into SpeI (compatible with BlnI) and XhoI digested C4-NHT to generate H45. H45 contained the CNTF gene joined to the hinge coding sequence which was in turn joined to the transferrin gene. (See FIG. 12E).

Figure 12F:
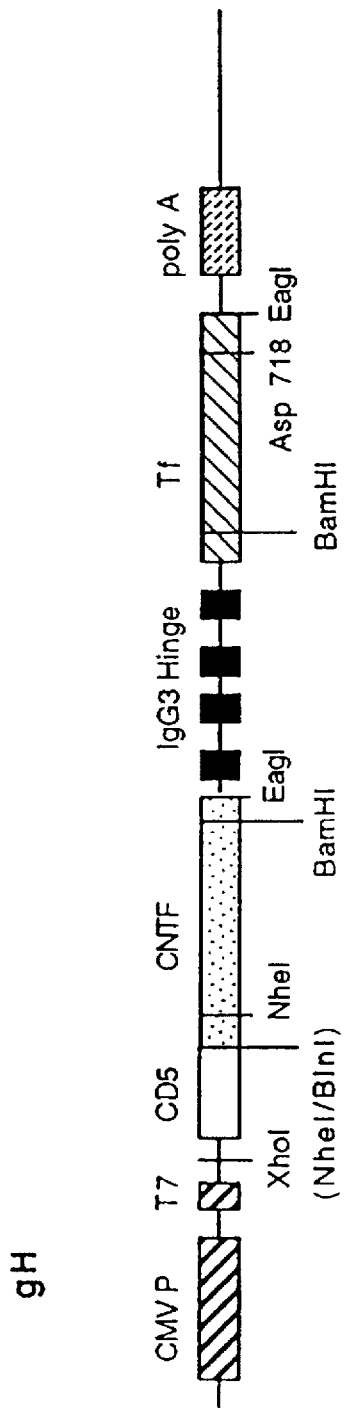
FIG. 12F is a restriction enzyme map of plasmid gH.

Finally, a 1.5 kb BamHI fragment from H45, which contained the 3' end of the CNTF gene, the hinge coding sequence and the 5' end of the transferrin gene, was isolated and cloned into BamHI digested g* to generate plasmid gH, a plasmid containing the CNTF-hinge-transferrin gene fusion downstream of the CMV promoter and the CD5 leader sequence. (See FIG. 12F).

B. CNTF-Transferrin Direct Fusion

The CNTF-transferrin direct fusion was made by a two step PCR procedure. In the first step, with J6 as the template, the CNTF coding sequence was amplified using primers P33.1 (SEQ.ID.NO.20, described above) and P38.1 (below), and the transferrin gene was amplified using primers P36.2 (below), P36.1 (SEQ. ID. NO. 23 described above) and template pcDNAI/AmpNHT. P38.1 was complementary to the 5' end of the transferrin gene and the 3' end of the CNTF coding sequence. P36.2 was complementary to the 3' end of the CNTF coding sequence and the 5' end of the transferrin gene.

```
P38.1
  5' end of transferrin/3' end of transferrin
  5'-CTCACAGTTTTATCAGGGAC CATTTTCTTGTTGTTAGC-3'
  (SEQ. ID. NO. 25)

P36.2
       3' end of CNTF        /    5' end of transferrin
  5'-GCTAACAACAAGAAAATG GTCCCTGATAAAACTGTG-3'
  (SEQ. ID. NO. 26)
```

The two amplified fragments were gel purified and equimolar amounts were combined for the second PCR using primers P33.1 and P36.1. The product, an intact fragment containing a CNTF-transferrin fusion gene, was digested with BlnI and EagI and ligated with NheI and EagI digested CD51neg1. A clone was identified by restriction analysis and designated A45. In order to minimize the possibility of mutations introduced by PCR, a BamHI fragment from A45, which spanned the joint between the CNTF and transferrin gene sequences, was cloned into BamHI digested g*. The resulting plasmid was designated gA.

C. CNTF-(Gly)$_5$-Transferrin Fusion

The CNTF-transferrin fusion separated by a series of nucleotides which encode five glycine residues was similarly constructed using two primer pairs and templates J6 and pcDNAI/AmpNHT. Primers P33.1 (SEQ. ID. NO. 20) and P53.2 (below) were complementary to the 5' and 3' ends of the CNTF gene. In addition, P53.2 contained an intervening nucleotide sequence encoding five glycines. Primers P53.1 (below) and P36.1 (SEQ. ID. NO. 23) were complementary to the 5' and 3' ends of the transferrin gene. P53.1 also contained the nucleotide sequence encoding five glycines and this sequence overlapped with the 3' ends of the fragment generated with primers P33.1 and P53.2.

```
P53.2
     5' end of transferrin            /    Gly$_5$
  5'-CTCACAGTTTTATCAGGGAC  CCCTCCACCTCC /      3' end of CNTF
  CCC CATTTTCTTGTTGTTAGC-3'
  (SEQ. ID. NO. 27)

P53.1
        3' end of CNTF/            Gly$_5$              /
  5'-GCTAACAACAAGAAAATG  GGGGGAGGTGGAGGG  GT 5' end of transferrin
  CCCTGATAAAACTGTGAG-3'
  (SEQ. ID. NO. 28)
```

After the first PCR reaction, the two amplified fragments were purified, annealed and subjected to a second round of PCR using primers P33.1 and P36.1. The final product was digested with BlnI and EagI and ligated with NheI and EagI digested CD51neg1 DNA. A clone was identified by restriction analysis and designated B45. The BamHI fragment was again exchanged for the BamHI fragment in g*, resulting in a plasmid designated gB.

Competition assays for transferrin receptor binding activity were performed as described in Example 11 to measure the affinity of the CNTF-transferrin fusion proteins for the human transferrin receptor. The results of these assays demonstrated that the CNTF-transferrin fusion proteins bind well to the human transferrin receptor.

A cell-based bioassay described by Collins et al. (1989, *Brain Res.* 502: pp. 99–108) was used to assay CNTF activity in the CNTF-transferrin fusions by measuring the ability of these fusion proteins to stimulate outgrowth of isolated neurons. The results of these bioassays demonstrated that all fusion proteins retained CNTF activity.

Equivalents

Those skilled in the art will know, or be able to ascertain using no more than routine experimentation, many equivalents to the specific embodiments expressly described herein. These are intended to be within the scope of the invention as described by the claims herein.

We claim:

1. A fusion protein comprising transferrin at the carboxyl terminus linked to a neuropharmaceutical agent at the amino terminus, wherein said neuropharmaceutical agent is either nerve growth factor (NGF) or ciliary neurotrophic factor (CNTF).

2. The fusion protein of claim 1 wherein transferrin and the neuropharmaceutical agent are linked through an intermediate polypeptide.

3. The fusion protein of claim 2 wherein the intermediate polypeptide is a segment of an antibody chain.

4. The fusion protein of claim 3 wherein the intermediate polypeptide is an IgG$_3$ hinge region.

5. The fusion protein of claim 4 wherein the neuropharmaceutical agent is nerve growth factor (NGF).

6. The fusion protein of claim 4 wherein the neuropharmaceutical agent is ciliary neurotrophic factor (CNTF).

7. The fusion protein of claim 2 wherein the intermediate polypeptide is a pentapeptide consisting of five glycines (gly)$_5$.

8. The fusion protein of claim 7 wherein the neuropharmaceutical agent is nerve growth factor (NGF).

9. The fusion protein of claim 7 wherein the neuropharmaceutical agent is ciliary neurotrophic factor (CNTF).

10. The fusion protein of claim 2 wherein the intermediate polypeptide is a dipeptide consisting of leucine-glutamic acid (leu-glu).

11. The fusion protein of claim 10 wherein the neuropharmaceutical agent is nerve growth factor (NGF).

* * * * *

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GGGTCGACCT CGAGGGTGAG AGGCCAGC      28

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GGAGTTACTC AGATCTGGGA AG      22

( 2 ) INFORMATION FOR SEQ ID NO:3:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GAAGCTTCTC GAGTCTAGAC CAGGTGCATA GCGTAATGTC C      41

( 2 ) INFORMATION FOR SEQ ID NO:4:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CGTCGACCTC GAGTCTCACA GCCTTCCTGC TGAGC      35

( 2 ) INFORMATION FOR SEQ ID NO:5:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:5:

```
CGTCGACTCT AGATTATCTC ACAGCCTTC                                              29
```

( 2 ) INFORMATION FOR SEQ ID NO:6:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:6:

```
TCCCCCGGGT CTAGACCAGG TGCATCCACC ATGTCCATGT TGTTC                            45
```

( 2 ) INFORMATION FOR SEQ ID NO:7:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:7:

```
AACAGCTATG ACCATG                                                            16
```

( 2 ) INFORMATION FOR SEQ ID NO:8:

( i ) SEQUENCE CHARACTERISTICS:
    ( A ) LENGTH: 1459 base pairs
    ( B ) TYPE: nucleic acid
    ( C ) STRANDEDNESS: double
    ( D ) TOPOLOGY: circular ( i i ) MOLECULE TYPE: DNA (genomic)

( v i ) ORIGINAL SOURCE:
    ( B ) STRAIN: CD5Inegl ( v i i i ) POSITION IN GENOME:
    ( A ) CHROMOSOME/SEGMENT: CD5 Leader; IgG1 Exon 1; IgG1 Exon 2; IgG1 Exon 3
    ( B ) MAP POSITION: 97-177; 535-593; 698-1027; 1124-1444

( x i ) SEQUENCE DESCRIPTION: SEQ ID NO:8:

```
CTCGAGATCC ATTGTGCTCT AAAGGAGATA CCCGGCCAGA CACCCTCACC TGCGGTGCCC           60
AGCTGCCCAG GCTGAGGCAA GAGAAGGCCA GAAACCATGC CCATGGGGTC TCTGCAACCG          120
CTGGCCACCT TGTACCTGCT GGGGATGCTG GTCGCTTCCG TGCTAGCGGA TCCCGAGGGT          180
GAGTACTAAG CTTCAGCGCT CCTGCCTGGA CGCATCCCGG CTATGCAGCC CCAGTCCAGG          240
GCAGCAAGGC AGGCCCCGTC TGCCTCTTCA CCCGGAGCCT CTGCCCGCCC CACTCATGCT          300
CAGGGAGAGG GTCTTCTGGC TTTTTCCCAG GCTCTGGGCA GGCACAGGCT AGGTGCCCCT          360
AACCCAGGCC CTGCACACAA AGGGGCAGGT GCTGGGCTCA GACCTGCCAA GAGCCATATC          420
```

```
CGGGAGGACC CTGCCCCTGA CCTAAGCCCA CCCCAAAGGC CAAACTCTCC ACTCCCTCAG        480

CTCGGACACC TTCTCTCCTC CCAGATTCCA GTAACTCCCA ATCTTCTCTC TGCAGAGCCC        540

AAATCTTGTG ACAAAACTCA CACATGCCCA CCGTGCCCAG GTAAGCCAGC CCAGGCCTCG        600

CCCTCCAGCT CAAGGCGGGA CAGGTGCCCT AGAGTAGCCT GCATCCAGGG ACAGGCCCCA        660

GCCGGGTGCT GACACGTCCA CCTCCATCTC TTCCTCAGCA CCTGAACTCC TGGGGGGACC        720

GTCAGTCTTC CTCTTCCCCC CAAAACCCAA GGACACCCTC ATGATCTCCC GGACCCCTGA        780

GGTCACATGC GTGGTGGTGG ACGTGAGCCA CGAAGACCCT GAGGTCAAGT TCAACTGGTA        840

CGTGGACGGC GTGGAGGTGC ATAATGCCAA GACAAAGCCG CGGGAGGAGC AGTACAACAG        900

CACGTACCGG GTGGTCAGCG TCCTCACCGT CCTGCACCAG GACTGGCTGA ATGGCAAGGA        960

GTACAAGTGC AAGGTCTCCA ACAAAGCCCT CCCAGCCCCC ATCGAGAAAA CCATCTCCAA       1020

AGCCAAAGGT GGGACCCGTG GGGTGCGAGG GCCACATGGA CAGAGGCCGG CTCGGCCCAC       1080

CCTCTGCCCT GAGAGTGACC GCTGTACCAA CCTCTGTCCT ACAGGGCAGC CCCGAGAACC       1140

ACAGGTGTAC ACCCTGCCCC CATCCCGGGA TGAGCTGACC AAGAACCAGG TCAGCCTGAC       1200

CTGCCTGGTC AAAGGCTTCT ATCCCAGCGA CATCGCCGTG GAGTGGGAGA GCAATGGGCA       1260

GCCGGAGAAC AACTACAAGA CCACGCCTCC CGTGCTGGAC TCCGACGGCT CCTTCTTCCT       1320

CTACAGCAAG CTCACCGTGG ACAAGAGCAG GTGGCAGCAG GGGAACGTCT TCTCATGCTC       1380

CGTGATGCAT GAGGCTCTGC ACAACCACTA CACGCAGAAG AGCCTCTCCC TGTCTCCGGG       1440

TAAATGAGTG CGACGGCCG                                                    1459
```

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
AAGGAGGTGA TGGTGTTGGG A                                                   21
```

( 2 ) INFORMATION FOR SEQ ID NO:10:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
CTCACAGTTT TATCAGGGAC TCTCACAGCC TTCCTGCTGA GC                             42
```

( 2 ) INFORMATION FOR SEQ ID NO:11:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
CAGCAGGAAG GCTGTGAGAG TCCCTGATAA AACTGTGAGA TG                             42
```

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
GTGTGGCAGG ACTTCTTGCC T                                         21
```

( 2 ) INFORMATION FOR SEQ ID NO:13:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
CAGCAGGAAG GCTGTGAGAG GGGGAGGTGG AGGGGTCCCT GATAAAACTG TGAGATG   57
```

( 2 ) INFORMATION FOR SEQ ID NO:14:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
CTCACAGTTT TATCAGGGAC CCCTCCACCT CCCCCTCTCA CAGCCTTC            48
```

( 2 ) INFORMATION FOR SEQ ID NO:15:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
GGAACGGCCT CGAGGTCCCT GATAAAACTG TGAGA                          35
```

( 2 ) INFORMATION FOR SEQ ID NO:16:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

```
AGTTAACATA TGGCTTTTAC TGAGCATTCA C                              31
```

( 2 ) INFORMATION FOR SEQ ID NO:17:

( i ) SEQUENCE CHARACTERISTICS:

```
            ( A ) LENGTH: 39 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:17:
```

CAGGCCCTGA TGCTTCACAT AGGATTCCGT AAGAGCAGT                                  39

( 2 ) INFORMATION FOR SEQ ID NO:18:

```
    ( i ) SEQUENCE CHARACTERISTICS:
            ( A ) LENGTH: 35 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:18:
```

TACGGAATCC TATGTGAAGC ATCAGGGCCT GAACA                                      35

( 2 ) INFORMATION FOR SEQ ID NO:19:

```
    ( i ) SEQUENCE CHARACTERISTICS:
            ( A ) LENGTH: 42 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:19:
```

GGGCCCTCGA GGGACTAACT GCTACATTTT CTTGTTGTTA GC                              42

( 2 ) INFORMATION FOR SEQ ID NO:20:

```
    ( i ) SEQUENCE CHARACTERISTICS:
            ( A ) LENGTH: 33 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:20:
```

CGCGGGCCTA GGCGCTTTCA CAGAGCATTC ACC                                        33

( 2 ) INFORMATION FOR SEQ ID NO:21:

```
    ( i ) SEQUENCE CHARACTERISTICS:
            ( A ) LENGTH: 38 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:21:
```

CGCGGGGCGG CCGCTTTACA TTTTCTTGTT GTTGTTAG                                   38

( 2 ) INFORMATION FOR SEQ ID NO:22:

```
    ( i ) SEQUENCE CHARACTERISTICS:
            ( A ) LENGTH: 33 base pairs
            ( B ) TYPE: nucleic acid
            ( C ) STRANDEDNESS: single
            ( D ) TOPOLOGY: linear
```

( i i ) MOLECULE TYPE: DNA (genomic)

( x i ) SEQUENCE DESCRIPTION: SEQ ID NO:22:

GCTTCCGTCC TAGGGGTCCC TGATAAAACT GTG    33

(2) INFORMATION FOR SEQ ID NO:23:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

CGCGGGGCGG CCGCTTTAAG GTCTACGGAA AGTGCA    36

(2) INFORMATION FOR SEQ ID NO:24:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

TGGCCTCTCA CCCTCGAGCA TTTTCTTGTT GTTAGC    36

(2) INFORMATION FOR SEQ ID NO:25:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

CTCACAGTTT TATCAGGGAC CATTTCTTG TTGTTAGC    38

(2) INFORMATION FOR SEQ ID NO:26:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

GCTAACAACA AGAAAATGGT CCCTGATAAA ACTGTG    36

(2) INFORMATION FOR SEQ ID NO:27:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

CTCACAGTTT TATCAGGGAC CCCTCCACCT CCCCCCATTT TCTTGTTGTT AGC    53

(2) INFORMATION FOR SEQ ID NO:28:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

GCTAACAACA AGAAAATGGG GGGAGGTGGA GGGGTCCCTG ATAAAACTGT GAG    53